(12) United States Patent
McBride et al.

(10) Patent No.: US 9,783,515 B2
(45) Date of Patent: Oct. 10, 2017

(54) RADIOMITIGATING PHARMACEUTICAL FORMULATIONS

(71) Applicant: The Regents of the University of California, Oakland, CA (US)

(72) Inventors: William McBride, Los Angeles, CA (US); Ewa Micewicz, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/889,719

(22) PCT Filed: May 7, 2014

(86) PCT No.: PCT/US2014/037110
§ 371 (c)(1),
(2) Date: Nov. 6, 2015

(87) PCT Pub. No.: WO2014/182789
PCT Pub. Date: Nov. 13, 2014

(65) Prior Publication Data
US 2016/0090369 A1   Mar. 31, 2016

Related U.S. Application Data

(60) Provisional application No. 61/820,447, filed on May 7, 2013.

(51) Int. Cl.
| | | |
|---|---|---|
| C07D 295/26 | (2006.01) | |
| C07D 401/04 | (2006.01) | |
| C07D 211/54 | (2006.01) | |
| C07D 215/54 | (2006.01) | |
| C07D 211/96 | (2006.01) | |
| C07D 333/34 | (2006.01) | |
| C07D 311/16 | (2006.01) | |
| C07C 311/16 | (2006.01) | |

(52) U.S. Cl.
CPC .......... *C07D 295/26* (2013.01); *C07C 311/16* (2013.01); *C07D 211/54* (2013.01); *C07D 211/96* (2013.01); *C07D 215/54* (2013.01); *C07D 333/34* (2013.01); *C07D 401/04* (2013.01)

(58) Field of Classification Search
CPC ... C07C 311/16; C07D 211/54; C07D 211/96; C07D 215/54; C07D 295/26; C07D 333/34; C07D 401/04
See application file for complete search history.

(56) References Cited

U.S. PATENT DOCUMENTS

| | | |
|---|---|---|
| 4,159,331 A | 6/1979 | McCall |
| 6,407,120 B1 | 6/2002 | Carpino et al. |
| 2003/0220326 A1 | 11/2003 | Chong et al. |
| 2004/0138206 A1 | 7/2004 | Chung et al. |
| 2005/0234033 A1 | 10/2005 | Anandan et al. |
| 2008/0207621 A1 | 8/2008 | Gless |
| 2016/0221976 A1* | 8/2016 | McBride .............. C07D 401/04 |

FOREIGN PATENT DOCUMENTS

| | | |
|---|---|---|
| WO | WO-2006/065646 A1 | 6/2006 |
| WO | WO-2006/068669 A1 | 6/2006 |
| WO | WO-2007/029078 A2 | 3/2007 |
| WO | WO-2007/143745 A2 | 12/2007 |
| WO | WO-2010/003023 A2 | 1/2010 |
| WO | WO-2010/023445 A1 | 3/2010 |
| WO | WO-2010/111713 A2 | 9/2010 |
| WO | WO-2012/112851 A2 | 8/2012 |

OTHER PUBLICATIONS

Norager, et al. Development of Potent Fluorescent Polyamine Toxins and Application in Labeling of Ionotropic Glutamate Receptors in Hippocampal Neurons, ACS Chem. Biol., 2013, 8 (9), pp. 2033-2041.*
Luo, et al., Chinese Chem. Let., vol. 20, No. 11, pp. 789-92 (2009).*
Martyn, et al., Antiplasmodial Activity of Piperazine Sulfonamides, Bioorganic & Med. Chem. Let. 20, 218-21 (2010).*
Kim, et al., Bull. Korean Chem. Soc., vol. 24, No. 11, pp. 1655-1658 (2003).*
International Search Report from related international application PCT/US2014/037110, dated Oct. 31, 2014.
Kim, H.K. et al., "Chemoselective N-benzenesul fonylation of aliphatic amines," B Kor Chem Soc, 24:1655-8 (2003).
Luo, Z.G. et al., "Synthesis of 6-sulfamoyl-4-oxoquinoline-3-carboxylic acid derivatives as integrase antagonists with anti-HIV activity," Chinese Chem Lett, 20:789-92 (2009).
Martyn, D.C. et al., "Antiplasmodial activity of piperazine sulfonamides," Bioorg Med Chem Lett, 20:218-221 (2010).
Belsito, et al., "N-(4-nitrophenylsulfonyl)- and N-(fluorenylmethoxycarbonyl)-N-ethyl amino," Eur J Org Chem, 22: 4245-4252 (2010).
Shaw, et al., "Pharmacological exploitation of the alpha1-adrenoreceptor antagonist doxazosin to develop a novel class of antitumor agents that block intracellular protein kinase B/Akt activation," J Med Chem, 47: 4453-4462 (2004).
Shi, et al., "Applying small molecule microarrays and resulting affinity probe cocktails," Chemistry—An Asian Journal, 10: 2803-2815 (2011).
Office Action from U.S. Appl. No. 15/094,192, dated Dec. 1, 2016.
Farr, et al., "Enantiospecific and regioselective opening of 2-alkyl nosylaziridines by indoles mediated by boron trifluoride. Application to a practical synthesis of a GnRH antagonist," Tetrahedron Asymmetry, 14(22): 3503-3515 (2003).

(Continued)

*Primary Examiner* — Erich A Leeser
(74) *Attorney, Agent, or Firm* — Foley Hoag LLP

(57) ABSTRACT

The present disclosure relates to compounds of Formula (I) and (II), compositions containing the compounds (alone or in combination with other agents), and their use to prevent, mitigate or treat a) damage induced by ionizing radiation, b) inflammation or c) cancer.

44 Claims, 16 Drawing Sheets

(56) References Cited

OTHER PUBLICATIONS

Gareau, et al., "Oxidation of aromatic and alipathic triisopropylsilanylsulfanyls to sulfonyl chlorides: preparation of sulfonamides," Tetrahedron Letters, 44(42): 7821-7824 (2003).
Idoux, et al., "Aromatic fluoroalkoxylation via direct displacement of a nitro or fluoro group," J Org Chem, 50(11): 1876-1878 (1985).
Liang, et al., "Novel N-dealkylation of N-alkylsulfonamides and N,N-dialkyl sulfonamides with periodic acid catalyzed by chromium (III) acetate hydroxide," Synlett, 11: 1901-1904 (2004).
Malik, et al., "Microwave-assisted efficient methylation of alkyl and arenesulfonamides with trimethylsulfoxonium iodide and KOH," Synthetic Communications, 38(1): 3074-3081 (2008).
Mukaiyama, et al., "A new method for the preparation of nitrogen-containing cyclic compounds from p-Nitrobenzenesulfonamide and alkyl bis(diphenylphosphonite)s by oxydation-reduction condensation using 1-aziodoadamante," Chem Lett, 34(12): 1644-1645 (2005).
Parai, et al., "Design, synthesis and antimalarial activity of benzene and isoquinoline sulfonamide derivatives," Bioorg Med Chem Lett, 18: 776-781 (2007).

\* cited by examiner

A.

D.

B.

E.

C.

- Control
- 75 mg/kg
- 40 mg/kg
- 5 mg/kg

A.

B.

A.

B.

A.

B.

A.

B.

RADIOMITIGATING PHARMACEUTICAL FORMULATIONS

RELATED APPLICATIONS

This application is the U.S. National Stage of International Patent Application No. PCT/US2014/037110, filed May 7, 2014, which claims the benefit of priority to U.S. Provisional Patent Application No. 61/820,447, filed May 7, 2013, the contents of both of which are hereby incorporated by reference in their entirety.

STATEMENT REGARDING FEDERALLY SPONSORED RESEARCH OR DEVELOPMENT

This invention was made with Government support under AI067769, awarded by the National Institutes of Health. The Government has certain rights in the invention.

BACKGROUND

Radiomitigation

The tragic nuclear power plant accidents in Fukushima, Japan caused severe leaks of radioactive Iodine-131 and Cesium-137 and a subsequent widespread exposure scare of radiation. In addition, the global use and storage of radioactivity is increasing rapidly. Millions of radioactive sealed sources are used around the world for legitimate and beneficial commercial applications such as cancer treatment, food and blood sterilization, oil exploration, remote electricity generation, radiography, and scientific research. These applications use isotopes such as Cesium-137, Cobalt-60, Strontium-90, Americium-241, Iridium-192, Plutonium-238, Plutonium-239, Curium-244, Radium-226, and Californium-252. Many of these radiological sources at sites around the world are no longer needed and have been abandoned or orphaned; others are poorly guarded, making the risk of theft or sabotage significant. Currently, there are tens of thousands of civilian locations worldwide with radioactive material, about 5,000 of which contain sources of 1,000 curies or greater (Office of Global Threat Reduction (NA-21), GTRI Strategic Plan, release date January 2007. 955 L'Enfant Plaza, Washington, D.C. 20585. Iliopulos, Ioanna et al. The Office of Global Threat Reduction: reducing the global threat from radiological dispersal devices. 2007. JNMM Volume 35 Issue 3 PP 36-40). Beyond the public safety concerns are the clinical implications of radiation use.

Outside the radiation therapy clinic there is also significant relevance to identifying and characterizing novel compounds that protect cells from radiation induced cell death.

Fundamental to radiation exposure and injury is DNA strand breaks, resulting in genetic instability and DNA deletions which are involved in cell death, cellular dysfunction, as well as long-term consequences such as birth defects and cancer.

Discovery of compounds that are capable of mitigating the process of normal tissue damage from radiation during radiotherapy, accidents, or terrorist attacks is of importance. Most currently available treatments for radiation exposure are free radical scavengers that reduce initial radiation-induced DNA damage and work best if added just before or at the time of irradiation. Because of this, these compounds are not practical countermeasures in a radiation incident. In that case, the search for radiomitigators—agents with robust, prolonged efficacy, broad specificity, and minimal toxicity that could protect a large population in the event of a radiological emergency is of importance.

SUMMARY OF THE INVENTION

The present invention provides compounds having structures as disclosed herein. Preferred compounds are radiomitigating, and thus can be used in the prevention, mitigation and treatment of radiation injury, and other medical conditions related to exposure to ionizing radiation.

The subject compounds are also useful for treating or preventing inflammatory disease and for treating or preventing cancer or other hyperproliferative conditions.

In one aspect, the invention provides compounds represented by general formula I or a pharmaceutically acceptable salt, ester, or prodrug thereof:

Formula I wherein:

$A^5$ is a secondary or tertiary amine (i.e., thereby forming a sulfonamide), and $A^6$ is a substituted or unsubstituted and or heteroaryl group, preferably wherein the aryl or heteroaryl group bears at least one substituent including a nitro substitutent, e.g., disposed at a position distal to the sulfonyl.

In certain embodiments, $A^5$ is a heterocyclic amine, such as a piperidine, piperazine, or morpholine ring, while in other embodiments, the amine is acyclic and/or the nitrogen atom bound to the sulfonyl is not included in any ring that may be present in $A^5$.

In certain embodiments, the invention provides compounds represented by general formula II or a pharmaceutically acceptable salt, ester or prodrug thereof:

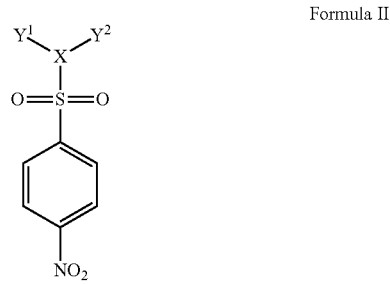

Formula II wherein:

X is N or —C(H)—, preferably N;

$Y^1$ and $Y^2$ are each independently lower alkyl or $Y^1$ and $Y^2$ taken together with X form a heterocyclyl ring system, such as

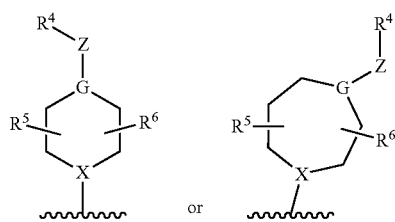

wherein

X is N;

G is selected from N or —C(H)—, preferably N;

Z is absent or selected from substituted or unsubstituted alkyl, heteroalkyl, alkenyl, or alkynyl; and R[4] is hydrogen or selected from substituted or unsubstituted aryl (e.g., phenyl) and heteroaryl, and R[5] and R[6] are each independently absent or lower alkyl.

In other embodiments, X, Y[1] and Y[2] taken together form a ring system

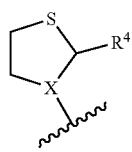

wherein X is —C(H)—, and

R[4] is selected from substituted or unsubstituted aryl (e.g., phenyl) and heteroaryl, such as a halogen-substituted phenyl group, e.g., 4-fluorophenyl or 3-chlorophenyl.

In certain embodiments, Y[1] and Y[2] are each ethyl.

In certain preferred embodiments, Y[1] and Y[2] taken together form a piperazine ring.

In certain preferred embodiments, Z is absent.

In certain embodiments, the compound of Formula II has a structure of one of compounds 1-7. However, in certain preferred embodiments of the compounds, compositions, uses, and methods disclosed herein, compounds 1-12 (or even compounds 1-12 and compounds P1, P2, and P3) are excluded.

In certain embodiments, compounds of the invention may be prodrugs of the compounds of formula I or II, e.g., wherein a hydroxyl in the parent compound is presented as an ester or a carbonate, or carboxylic acid present in the parent compound is presented as an ester. In certain such embodiments, the prodrug is metabolized to the active parent compound in vivo (e.g., the ester is hydrolyzed to the corresponding hydroxyl, or carboxylic acid).

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. In certain embodiments, compounds of the invention may have more than one stereocenter. In certain such embodiments, compounds of the invention may be enriched in one or more diastereomer. For example, a compound of the invention may have greater than 30% de, 40% de, 50% de, 60% de, 70% de, 80% de, 90% de, or even 95% or greater de.

In certain embodiments, the present invention relates to methods of treatment with a compound of formula I or II, or a pharmaceutically acceptable salt thereof. In certain embodiments, the therapeutic preparation may be enriched to provide predominantly one enantiomer of a compound (e.g., of formula I or II). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of formula I or II). A diastereomerically enriched mixture may comprise, for example, at least 60 mol percent of one diastereomer, or more preferably at least 75, 90, 95, or even 99 mol percent.

In certain embodiments, the present invention relates to methods of treatment with a compound of formula I or II, or a pharmaceutically acceptable salt thereof. In certain embodiments, the therapeutic preparation may be enriched to provide predominantly one enantiomer of a compound (e.g., of formula I or II). An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, the therapeutic preparation may be enriched to provide predominantly one diastereomer of a compound (e.g., of formula I or II). A diastereomerically enriched mixture may comprise, for example, at least 60 mol percent of one diastereomer, or more preferably at least 75, 90, 95, or even 99 mol percent.

In certain embodiments, the present invention provides a pharmaceutical preparation suitable for use in a human patient, comprising any of the compounds shown above (e.g., a compound of the invention, such as a compound of formula I or II), and one or more pharmaceutically acceptable excipients. In certain embodiments, the pharmaceutical preparations may be for use in treating or preventing a condition or disease as described herein. In certain embodiments, the pharmaceutical preparations have a low enough pyrogen activity to be suitable for use in a human patient.

Compounds of any of the above structures may be used in the manufacture of medicaments for the treatment of any diseases or conditions disclosed herein.

In certain embodiments, the compounds of Formula I or II mitigate tissue damage induced by exposure to ionizing radiation and/or inhibit inflammation.

In one aspect, the invention provides a pharmaceutical composition comprising a compound as disclosed herein and a pharmaceutically acceptable excipient or solvent. In certain embodiments, a pharmaceutical composition may comprise a prodrug of a compound as disclosed herein.

In another aspect, the invention provides a method of mitigating the effect of ionizing radiation on a cell, organ, tissue, or organism by contacting the cell, organ, tissue, or organism with at least one compound shown in Table 1. The cell, organ, tissue, or organism may be contacted with a compound shown in Table 1 before, during, or after exposure to ionizing radiation.

In some embodiments, the compound may be administered prophylactically, i.e., before exposure to ionizing radiation, for example, prior to cancer radiation therapy or X-ray. In some embodiments, the compound may be administered during exposure, or upon repeated exposure to ionizing radiation. In some embodiments, the compound may be administered after exposure to ionizing radiation, or after the initiation of exposure to radiation.

When administering a compound of Formula I or II to an organism, the compound may be administered by any suitable means. In some embodiments, the compounds or formulations are administered orally. In some embodiments, the compounds or formulations are administered by injection, e.g. subcutaneous, parenteral, or intravenous, injections. In some embodiments, the compound may be administered in combination with other potential mitigators. In certain embodiments, compounds of Formula I or II are administered in conjunction with other therapies, such as radiation therapy, other anti-inflammatory compounds, or other anticancer drugs.

In certain embodiments, a method of the invention may comprise contacting a cell with a prodrug of a compound as disclosed herein.

Definitions

The terms "a," "an," "the" and similar referents used in the context of describing the present invention are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any unclaimed element is essential to the practice of the invention.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group. An alkyl group with two open valences is sometimes referred to as an alkylene group, such as methylene, ethylene, propylene and the like.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamide, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamide, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively. As applied to heteroalkyls, "$C_{x-y}$" indicates that the group contains from x to y carbons and heteroatoms in the chain. As applied to carbocyclic structures, such as aryl and cycloalkyl groups, "$C_{x-y}$" indicates that the ring comprises x to y carbon atoms. As applied to heterocyclic structures, such as heteroaryl and heterocyclyl groups, "$C_{x-y}$" indicates that the ring contains from x to y carbons and heteroatoms. As applied to groups, such as aralkyl and heterocyclylalkyl groups, that have both ring and chain components, "$C_{x-y}$" indicates that the ring and the chain together contain from x to y carbon atoms and, as appropriate heteroatoms.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl carbocyclyl, aryl, heterocyclyl, or heteroaryl groups is contemplated.

The term "amide", as used herein, refers to a group

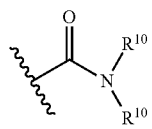

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

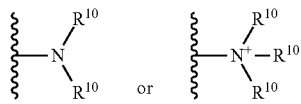

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

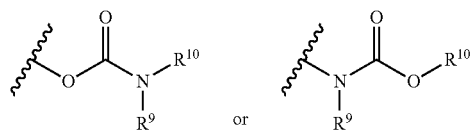

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle" and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2]heptane, 1,5-cyctooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—R$^{10}$, wherein R$^{10}$ represents a hydrocarbyl group.

The term "carboxy", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent. In analogy with alkyl groups, heteroalkyl groups with two open valences are sometimes referred to as heteroalkylene groups. Preferably, the heteroatoms in heteroalkyl groups are selected from O and N.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7. When a polycyclic substituent is attached through an aryl or heteroaryl ring, that substituent may be referred to herein as an aryl or heteroaryl group, while if the polycyclic substituent is attached through a cycloalkyl or heterocyclyl group, that substituent may be referred to herein as a cycloalkyl or heterocyclyl group. By way of example, a 1,2,3,4-tetrahydronaphthalen-1-yl group would be a cycloalkyl group, while a 1,2,3,4-tetrahydronaphthalen-5-yl group would be an aryl group.

The term "silyl" refers to a silicon moiety with three hydrocarbyl moieties attached thereto.

The term "substituted" refers to moieties having substituents replacing a hydrogen on one or more carbons or heteroatoms of the moiety. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds.

In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamide, a sulfonyl, a heterocyclyl, an aralkyl, or an aromatic or heteroaromatic moiety, it will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

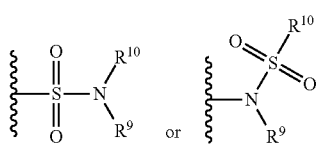

wherein $R^9$ and $R^{10}$ independently represents hydrogen or hydrocarbyl, such as alkyl, or $R^9$ and $R^{10}$ taken together with the intervening atom(s) complete a heterocycle having from 4 to 8 atoms in the ring structure.

The term "sulfoxide" is art-recognized and refers to the group —S(O)—$R^{10}$, wherein $R^{10}$ represents a hydrocarbyl.

The term "sulfonate" is art-recognized and refers to the group $SO_3H$, or a pharmaceutically acceptable salt thereof.

The term "sulfone" is art-recognized and refers to the group —S(O)$_2$—$R^{10}$, wherein $R^{10}$ represents a hydrocarbyl.

The term "thioalkyl", as used herein, refers to an alkyl group substituted with a thiol group.

The term "thioester", as used herein, refers to a group —C(O)S$R^{10}$ or —SC(O)$R^{10}$ wherein $R^{10}$ represents a hydrocarbyl.

The term "thioether", as used herein, is equivalent to an ether, wherein the oxygen is replaced with a sulfur.

The term "urea" is art-recognized and may be represented by the general formula

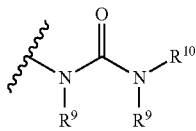

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxylprotecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I or II). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I or II in a formulation represented above can be replaced with the corresponding suitable prodrug, e.g., wherein a hydroxyl in the parent compound is presented as an ester or a carbonate or carboxylic acid present in the parent compound is presented as an ester.

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In a preferred embodiment, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch.

A pharmaceutical composition disclosed herein may comprise a therapeutic compound in an amount sufficient to allow customary administration to an individual. In certain embodiments, a pharmaceutical composition disclosed herein may comprise, e.g., at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 85 mg, at least 90 mg, at least 95 mg, or at least 100 mg of a therapeutic compound. In certain embodiments, a pharmaceutical composition disclosed herein may comprise, e.g., at least 5 mg, at least 10 mg, at least 20 mg, at least 25 mg, at least 50 mg, at least 75 mg, at least 100 mg, at least 200 mg, at least 300 mg, at least 400 mg, at least 500 mg, at least 600 mg, at least 700 mg, at least 800 mg, at least 900 mg, at least 1,000 mg, at least 1,100 mg, at least 1,200 mg, at least 1,300 mg, at least 1,400 mg, or at least 1,500 mg of a therapeutic compound. In yet other aspects of this embodiment, a pharmaceutical composition disclosed herein may comprise in the range of, e.g., about 5 mg to about 100 mg, about 10 mg to about 100 mg, about 50 mg to about 150 mg, about 100 mg to about 250 mg, about 150 mg to about 350 mg, about 250 mg to about 500 mg, about 350 mg to about 600 mg, about 500 mg to about 750 mg, about 600 mg to about 900 mg, about 750 mg to about 1,000 mg, about 850 mg to about 1,200 mg, or about 1,000 mg to about 1,500 mg. In still certain embodiments, a pharmaceutical composition disclosed herein may comprise in the range of, e.g., about 10 mg to about 250 mg, about 10 mg to about 500 mg, about 10 mg to about 750 mg, about 10 mg to about 1,000 mg, about 10 mg to about 1,500 mg, about 50 mg to about 250 mg, about 50 mg to about 500 mg, about 50 mg to about 750 mg, about 50 mg to about 1,000 mg, about 50 mg to about 1,500 mg, about 100 mg to about 250 mg, about 100 mg to about 500 mg, about 100 mg to about 750 mg, about 100 mg to about 1,000 mg, about 100 mg to about 1,500 mg, about 200 mg to about 500 mg, about 200 mg to about 750 mg, about 200 mg to about 1,000 mg, about 200 mg to about 1,500 mg, about 5 mg to about 1,500 mg, about 5 mg to about 1,000 mg, or about 5 mg to about 250 mg.

A pharmaceutical composition disclosed herein may comprise a solvent, emulsion or other diluent in an amount sufficient to dissolve a therapeutic compound disclosed herein. In certain embodiments, a pharmaceutical composition disclosed herein may comprise a solvent, emulsion or a diluent in an amount of e.g., less than about 90% (v/v), less than about 80% (v/v), less than about 70% (v/v), less than about 65% (v/v), less than about 60% (v/v), less than about 55% (v/v), less than about 50% (v/v), less than about 45% (v/v), less than about 40% (v/v), less than about 35% (v/v), less than about 30% (v/v), less than about 25% (v/v), less than about 20% (v/v), less than about 15% (v/v), less than about 10% (v/v), less than about 5% (v/v), or less than about 1% (v/v). In certain embodiments, a pharmaceutical composition disclosed herein may comprise a solvent, emulsion or other diluent in an amount in a range of, e.g., about 1% (v/v) to 90% (v/v), about 1% (v/v) to 70% (v/v), about 1% (v/v) to 60% (v/v), about 1% (v/v) to 50% (v/v), about 1% (v/v) to 40% (v/v), about 1% (v/v) to 30% (v/v), about 1% (v/v) to 20% (v/v), about 1% (v/v) to 10% (v/v), about 2% (v/v) to 50% (v/v), about 2% (v/v) to 40% (v/v), about 2% (v/v) to 30% (v/v), about 2% (v/v) to 20% (v/v), about 2% (v/v) to 10% (v/v), about 4% (v/v) to 50% (v/v), about 4% (v/v) to 40% (v/v), about 4% (v/v) to 30% (v/v), about 4% (v/v) to 20% (v/v), about 4% (v/v) to 10% (v/v), about 6% (v/v) to 50% (v/v), about 6% (v/v) to 40% (v/v), about 6% (v/v) to 30% (v/v), about 6% (v/v) to 20% (v/v), about 6% (v/v) to 10% (v/v), about 8% (v/v) to 50% (v/v), about 8% (v/v) to 40% (v/v), about 8% (v/v) to 30% (v/v), about 8% (v/v) to 20% (v/v), about 8% (v/v) to 15% (v/v), or about 8% (v/v) to 12% (v/v).

The final concentration of a therapeutic compound disclosed herein in a pharmaceutical composition disclosed herein may be of any suitable concentration. In certain embodiments, the final concentration of a therapeutic compound in a pharmaceutical composition may be a therapeutically effective amount. In certain embodiments, the final concentration of a therapeutic compound in a pharmaceutical composition may be, e.g., at least 0.00001 mg/mL, at least 0.0001 mg/mL, at least 0.001 mg/mL, at least 0.01 mg/mL, at least 0.1 mg/mL, at least 1 mg/mL, at least 10 mg/mL, at least 25 mg/mL, at least 50 mg/mL, at least 100 mg/mL, at least 200 mg/mL, at least 500 mg/mL, at least 700 mg/mL, at least 1,000 mg/mL, or at least 1,200 mg/mL. In certain embodiments, the concentration of a therapeutic compound disclosed herein in the solution may be, e.g., at most 1,000 mg/mL, at most 1,100 mg/mL, at most 1,200 mg/mL, at most 1,300 mg/mL, at most 1,400 mg/mL, at most 1,500 mg/mL, at most 2,000 mg/mL, at most 2,000 mg/mL, or at most 3,000 mg/mL. In certain embodiments, the final concentration of a therapeutic compound in a pharmaceutical composition may be in a range of, e.g., about 0.00001 mg/mL to about 3,000 mg/mL, about 0.0001 mg/mL to about 3,000 mg/mL, about 0.01 mg/mL to about 3,000 mg/mL, about 0.1 mg/mL to about 3,000 mg/mL, about 1 mg/mL to about 3,000 mg/mL, about 250 mg/mL to about 3,000 mg/mL, about 500 mg/mL to about 3,000 mg/mL, about 750 mg/mL to about 3,000 mg/mL, about 1,000 mg/mL to about 3,000 mg/mL, about 100 mg/mL to about 2,000 mg/mL, about 250 mg/mL to about 2,000 mg/mL, about 500 mg/mL to about 2,000 mg/mL, about 750 mg/mL to about 2,000 mg/mL, about 1,000 mg/mL to about 2,000 mg/mL, about 100 mg/mL to about 1,500 mg/mL, about 250 mg/mL to about 1,500 mg/mL, about 500 mg/mL to about 1,500 mg/mL, about 750 mg/mL to about 1,500 mg/mL, about 1,000 mg/ml, to about 1,500 mg/mL, about 100 mg/mL to about 1,200 mg/mL, about 250 mg/mL to about 1,200 mg/mL, about 500 mg/mL to about 1,200 mg/mL, about 750 mg/mL to about 1,200 mg/mL, about 1,000 mg/mL to about 1,200 mg/mL, about 100 mg/mL to about 1,000 mg/mL, about 250 mg/mL to about 1,000 mg/mL, about 500 mg/mL to about 1,000 mg/mL, about 750 mg/mL to about 1,000 mg/mL, about 100 mg/mL to about 750 mg/mL, about 250 mg/mL to about 750 mg/mL, about 500 mg/mL to about 750 mg/mL, about 100 mg/mL to about 500 mg/mL, about 250 mg/mL to about 500 mg/mL, about 0.00001 mg/mL to about 0.0001 mg/mL, about 0.00001 mg/mL to about 0.001 mg/mL, about 0.00001 mg/mL to about 0.01 mg/mL, about 0.00001 mg/mL to about 0.1 mg/mL, about 0.00001 mg/mL to about 1 mg/mL, about 0.001 mg/mL to about 0.01 mg/mL, about 0.001 mg/mL to about 0.1 mg/mL, about 0.001 mg/mL to about 1 mg/mL, about 0.001 mg/mL to about 10 mg/mL, or about 0.001 mg/mL to about 100 mg/mL.

In certain embodiments, a therapeutically effective amount of a therapeutic compound disclosed herein generally is in the range of about 0.001 mg/kg/day to about 100 mg/kg/day. In certain embodiments, an effective amount of a therapeutic compound disclosed herein may be, e.g., at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day. In certain embodiments, an effective amount of a therapeutic compound disclosed herein may be in the range of, e.g., about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In yet other aspects of this embodiment, an effective amount of a therapeutic compound disclosed herein may be in the range of, e.g., about 0.01 mg/kg/day to about 10 mg/kg/day, about 0.01 mg/kg/day to about 15 mg/kg/day, about 0.01 mg/kg/day to about 20 mg/kg/day, about 0.01 mg/kg/day to about 25 mg/kg/day, about 0.01 mg/kg/day to about 30 mg/kg/day, about 0.01 mg/kg/day to about 35 mg/kg/day, about 0.01 mg/kg/day to about 40 mg/kg/day, about 0.01 mg/kg/day to about 45 mg/kg/day, about 0.01 mg/kg/day to about 50 mg/kg/day, about 0.01 mg/kg/day to about 75 mg/kg/day, or about 0.01 mg/kg/day to about 100 mg/kg/day. In certain embodiments, an effective amount of a therapeutic compound disclosed herein may be in the range of, e.g., about 0.1 mg/kg/day to about 10 mg/kg/day, about 0.1 mg/kg/day to about 15 mg/kg/day, about 0.1 mg/kg/day to about 20 mg/kg/day, about 0.1 mg/kg/day to about 25 mg/kg/day, about 0.1 mg/kg/day to about 30 mg/kg/day, about 0.1 mg/kg/day to about 35 mg/kg/day, about 0.1 mg/kg/day to about 40 mg/kg/day, about 0.1 mg/kg/day to about 45 mg/kg/day, about 0.1 mg/kg/day to about 50 mg/kg/day, about 0.1 mg/kg/day to about 75 mg/kg/day, or about 0.1 mg/kg/day to about 100 mg/kg/day.

In other aspects of this embodiment, an effective amount of a therapeutic compound disclosed herein may be in the range of, e.g., about 1 mg/kg/day to about 10 mg/kg/day, about 1 mg/kg/day to about 15 mg/kg/day, about 1 mg/kg/day to about 20 mg/kg/day, about 1 mg/kg/day to about 25 mg/kg/day, about 1 mg/kg/day to about 30 mg/kg/day, about 1 mg/kg/day to about 35 mg/kg/day, about 1 mg/kg/day to about 40 mg/kg/day, about 1 mg/kg/day to about 45 mg/kg/day, about 1 mg/kg/day to about 50 mg/kg/day, about 1 mg/kg/day to about 75 mg/kg/day, or about 1 mg/kg/day to about 100 mg/kg/day. In certain embodiments, an effective amount of a therapeutic compound disclosed herein may be in the range of, e.g., about 5 mg/kg/day to about 10 mg/kg/day, about 5 mg/kg/day to about 15 mg/kg/day, about 5 mg/kg/day to about 20 mg/kg/day, about 5 mg/kg/day to about 25 mg/kg/day, about 5 mg/kg/day to about 30 mg/kg/day, about 5 mg/kg/day to about 35 mg/kg/day, about 5 mg/kg/day to about 40 mg/kg/day, about 5 mg/kg/day to about 45 mg/kg/day, about 5 mg/kg/day to about 50 mg/kg/day, about 5 mg/kg/day to about 75 mg/kg/day, or about 5 mg/kg/day to about 100 mg/kg/day.

In liquid and semi-solid formulations, a concentration of a therapeutic compound disclosed herein typically may be between about 50 mg/mL to about 1,000 mg/mL. In certain embodiments, a therapeutically effective amount of a therapeutic disclosed herein may be from, e.g., about 50 mg/ml, to about 100 mg/mL, about 50 mg/mL to about 200 mg/mL, about 50 mg/mL to about 300 mg/mL, about 50 mg/mL to about 400 mg/mL, about 50 mg/mL to about 500 mg/mL, about 50 mg/mL to about 600 mg/mL, about 50 mg/mL to about 700 mg/mL, about 50 mg/mL to about 800 mg/mL, about 50 mg/mL to about 900 mg/mL, about 50 mg/mL to about 1,000 mg/mL, about 100 mg/mL to about 200 mg/mL, about 100 mg/mL to about 300 mg/mL, about 100 mg/mL to about 400 mg/mL, about 100 mg/mL to about 500 mg/mL, about 100 mg/mL to about 600 mg/mL, about 100 mg/mL to about 700 mg/mL, about 100 mg/mL to about 800 mg/mL, about 100 mg/mL to about 900 mg/mL, about 100 mg/mL to about 1,000 mg/mL, about 200 mg/mL to about 300 mg/mL, about 200 mg/mL to about 400 mg/mL, about 200 mg/mL to about 500 mg/mL, about 200 mg/mL to about 600 mg/mL, about 200 mg/mL to about 700 mg/mL, about 200 mg/mL to about 800 mg/mL, about 200 mg/mL to about 900 mg/mL, about 200 mg/mL to about 1,000 mg/mL, about 300 mg/mL to about 400 mg/mL, about 300 mg/mL to about 500 mg/mL, about 300 mg/mL to about 600 mg/mL, about 300 mg/mL to about 700 mg/mL, about 300 mg/mL to about 800 mg/mL, about 300 mg/mL to about 900 mg/mL, about 300 mg/mL to about 1,000 mg/mL, about 400 mg/mL to about 500 mg/mL, about 400 mg/mL to about 600 mg/mL, about 400 mg/mL to about 700 mg/mL, about 400 mg/mL to about 800 mg/mL, about 400 mg/mL to about 900 mg/mL, about 400 mg/mL to about 1,000 mg/mL, about 500 mg/mL to about 600 mg/mL, about 500 mg/mL to about 700 mg/mL, about 500 mg/mL to about 800 mg/mL, about 500 mg/mL to about 900 mg/mL, about 500 mg/mL to about 1,000 mg/mL, about 600 mg/mL to about 700 mg/mL, about 600 mg/mL to about 800 mg/mL, about 600 mg/mL to about 900 mg/mL, or about 600 mg/mL to about 1,000 mg/mL.

DETAILED DESCRIPTION

Figure 1:
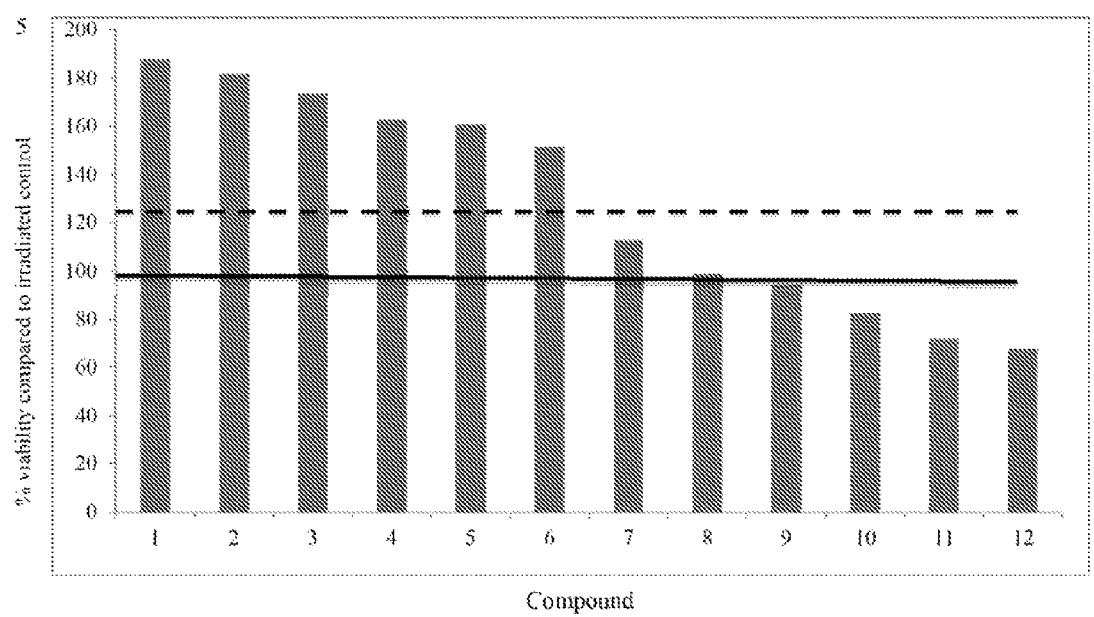
FIG. 1 shows the ability of certain compounds of the invention to mitigate radiation induced apoptosis in vitro relative to control values.
Figure 2:
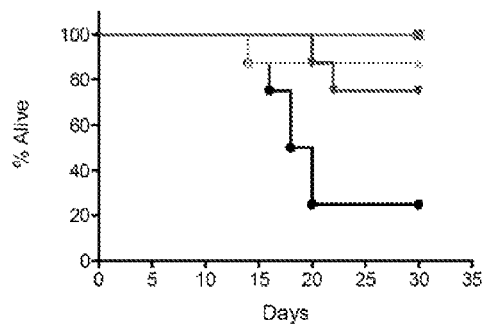
FIG. 2 shows the mitigation against whole body radiation lethality in vivo by compound 1 (FIG. 2A), compound 2 (FIG. 2B), compound 3 (FIG. 2C), compound 4 (FIG. 2D), compound 5 (FIG. 2E).
Figure 2:
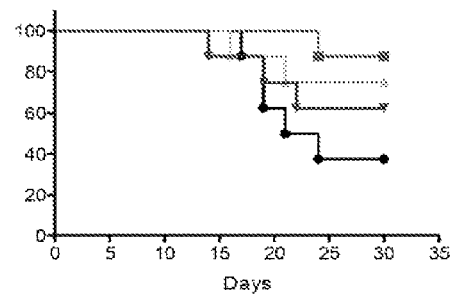
Figure 2:
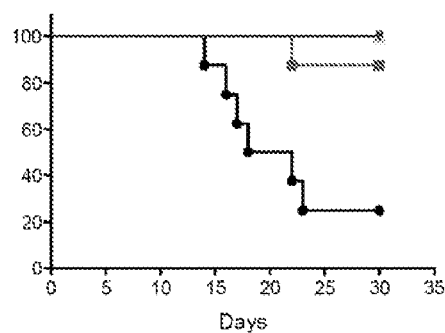
Figure 2:
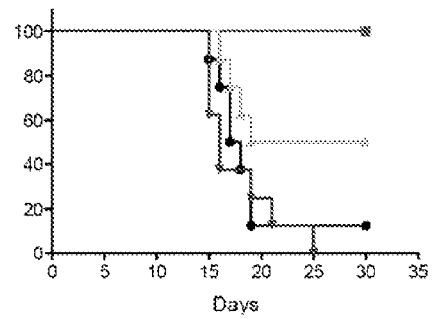
Figure 2:
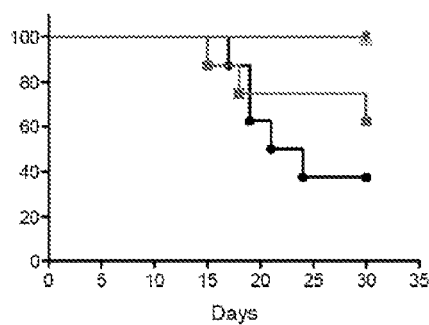

Compounds shown in Table 1 mitigate the effects of ionizing radiation, inhibit inflammation, and are useful for treating cancer and other hyperproliferative disorders. Pharmaceutical formulations using compounds shown in Table 1 have potential to improve the outcome of radiation exposure, and therefore they may be useful in the cancer radiotherapy, as well as in the situation of a radiological emergency.

Radiomitigation

Without wishing to be bound by theory, the compounds shown in Table 1 may protect against deleterious effects of ionizing radiation by promoting repair of DNA damage caused by exposure to radiation. The compounds also inhibit inflammation as well as protect bone marrow and other organs from radiation damage. As disclosed herein, after in vitro screening, the chosen compounds were applied in mice 24 hours after TBI and provided greatly elevated animals' survival level, compared to a control group. They also mitigated lethal normal gut and lung radiation damage, as well as having anti-tumor activity with and without therapeutic doses of ionizing radiation.

Embodiments of the invention include pharmaceutical formulations having a compound shown in Table 1, or pharmaceutically acceptable salt thereof, and at least one pharmaceutically acceptable carrier or diluent.

Embodiments of the invention include methods of mitigating the effect of ionizing radiation on a cell, organ, tissue, or organism by contacting the cell, organ, tissue, or organism with at least one compound shown in Table 1.

As used herein, "mitigating" means reducing the negative effects caused by exposure to ionizing radiation, relative to a cell, organ, tissue, or organism exposed to the same level of radiation for the same amount of time, but untreated.

In some embodiments, contacting the cell, organ, tissue, or organism with a compound in Table 1 may comprise administering a therapeutically effective amount of the compound to a subject.

As used herein, a "therapeutically effective amount" is an amount sufficient to mitigate the effects of the ionizing radiation.

The subject may be any organism that has been exposed to ionizing radiation, or which may be exposed to ionizing radiation. In one embodiment, the invention provides a method wherein the subject is a human, rat, mouse, cat, dog, horse, sheep, cow, monkey, avian, or amphibian. In another embodiment, the cell is in vivo or in vitro. Typical subjects to which compounds of the invention may be administered will be mammals, particularly primates, especially humans. For veterinary applications, a wide variety of subjects will be suitable, e.g. livestock such as cattle, sheep, goats, cows, swine and the like; poultry such as chickens, ducks, geese, turkeys, and the like; and domesticated animals particularly pets such as dogs and cats. For diagnostic or research applications, a wide variety of mammals will be suitable subjects including rodents (e.g. mice, rats, hamsters), rabbits, primates, and swine such as inbred pigs and the like. Additionally, for in vitro applications, such as in vitro diagnostic and research applications, body fluids and cell samples of the above subjects will be suitable for use such as mammalian, particularly primate such as human, blood, urine or tissue samples, or blood urine or tissue samples of the animals mentioned for veterinary applications.

The cell, organ, tissue, or organism may be contacted with a compound shown in Table 1 before, during, or after exposure to ionizing radiation. In some embodiments, the compound may be administered prophylactically, i.e. before exposure to ionizing radiation, for example, prior to cancer radiation therapy or X-ray. In some embodiments, the compound may be administered during exposure, or upon repeated exposure to ionizing radiation. In some embodiments, the compound may be administered after exposure to ionizing radiation, or after the initiation of exposure to radiation.

When administering to an organism, the compound may be administered by any suitable means. In some embodiments, the compounds or formulations are administered orally. In some embodiments, the compounds or formulations are administered by injection, e.g. subcutaneous, parenteral, or intravenous, injections. In some embodiments the compound may be administered in combination with other potential mitigators or with other toxic agents such as chemotherapeutic drugs.

Ionizing radiation may refer to radiation with a photon energy greater than 10 eV, according to the U.S. Federal Communications Commission, but for biological purposes may be considered to be radiation having energy greater than the first ionization potential of oxygen or the ionization potential of hydrogen, and may have other meanings according to practitioners.

Inflammatory Diseases

Compounds of the current invention may also be used for the treatment or prevention of inflammation and inflammatory diseases.

Examples of inflammatory conditions, which may be treated or prevented by the administration of a compound of the invention include, but are not limited to, inflammation of the lungs, joints, connective tissue, eyes, nose, bowel, kidney, liver, skin, central nervous system, vascular system and heart. In certain embodiments, inflammatory conditions which may be treated by the current invention include inflammation due to the infiltration of leukocytes or other immune effector cells into affected tissue. Other relevant examples of inflammatory conditions which may be treated by the present invention include inflammation caused by infectious agents, including, but not limited to, viruses, bacteria fungi and parasites.

Inflammatory lung conditions include, but are not limited to, asthma, adult respiratory distress syndrome, bronchitis, pulmonary inflammation, pulmonary fibrosis, and cystic fibrosis (which may additionally or alternatively involve the gastro-intestinal tract or other tissue(s)). Inflammatory joint conditions include rheumatoid arthritis, rheumatoid spondylitis, juvenile rheumatoid arthritis, osteoarthritis, gouty arthritis and other arthritic conditions. Eye diseases with an inflammatory component include, but are not limited to, uveitis (including iritis), conjunctivitis, scleritis, keratoconjunctivitis sicca, and retinal diseases, including, but not limited to, diabetic retinopathy, retinopathy of prematurity, retinitis pigmentosa, and dry and wet age-related macular degeneration. Inflammatory bowel conditions include Crohn's disease, ulcerative colitis and distal proctitis.

Inflammatory skin diseases include, but are not limited to, conditions associated with cell proliferation, such as psoriasis, eczema and dermatitis, (e.g., eczematous dermatitides, topic and seborrheic dermatitis, allergic or irritant contact dermatitis, eczema craquelee, photoallergic dermatitis, phototoxic dermatitis, phytophotodermatitis, radiation dermatitis, and stasis dermatitis). Other inflammatory skin diseases include, but are not limited to, scleroderma, ulcers and erosions resulting from trauma, burns, bullous disorders, or ischemia of the skin or mucous membranes, several forms of ichthyoses, epidermolysis bullosae, hypertrophic scars, keloids, cutaneous changes of intrinsic aging, photoaging, frictional blistering caused by mechanical shearing of the skin and cutaneous atrophy resulting from the topical use of corticosteroids. Additional inflammatory skin conditions include inflammation of mucous membranes, such as cheilitis, chapped lips, nasal irritation, mucositis and vulvovaginitis.

Inflammatory disorders of the endocrine system include, but are not limited to, autoimmune thyroiditis (Hashimoto's disease), Type I diabetes, and acute and chronic inflammation of the adrenal cortex. Inflammatory conditions of the cardiovascular system include, but are not limited to, coronary infarct damage, peripheral vascular disease, myocarditis, vasculitis, revascularization of stenosis, atherosclerosis, and vascular disease associated with Type II diabetes.

Inflammatory condition of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome and tubular ischemia.

Inflammatory conditions of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis.

Inflammatory conditions of the central nervous system include, but are not limited to, multiple sclerosis and neurodegenerative diseases such as Alzheimer's disease, Parkinson's disease, or dementia associated with HIV infection.

Other inflammatory conditions include periodontal disease, tissue necrosis in chronic inflammation, endotoxin shock, smooth muscle proliferation disorders, graft versus host disease, tissue damage following ischemia reperfusion injury, and tissue rejection following transplant surgery.

The present invention further provides a method of treating or preventing inflammation associated with post-surgical wound healing in a patient comprising administering to said patient a compound of the invention.

It should be noted that compounds of the current invention may be used to treat or prevent any disease which has an inflammatory component, such as those diseases cited above. Further, the inflammatory conditions cited above are meant to be exemplary rather than exhaustive.

Those skilled in the art would recognize that additional inflammatory conditions (e.g., systemic or local immune imbalance or dysfunction due to an injury, an insult, infection, inherited disorder, or an environmental intoxicant or perturbant to the subject's physiology) may be treated or prevented by compounds of the current invention. Thus, the methods of the current invention may be used to treat or prevent any disease which has an inflammatory component, including, but not limited to, those diseases cited above.

The present invention also provides methods for treating or preventing arthritis, inflammatory bowel disease, uveitis, ocular inflammation, asthma, pulmonary inflammation, cystic fibrosis, psoriasis, arterial inflammation, cardiovascular diseases, multiple sclerosis, or neurodegenerative disease by administering an effective amount of a compound of the invention.

The present invention also provides methods for treating ischemia by administering an effective amount of a compound of the invention. In certain embodiments, the ischemia is cardiac ischemia, cerebral ischemia, bowel ischemia (e.g., ischemic colitis or mesenteric ischemia), or cutaneous ischemia.

Cancer

Compounds of the current invention may also be used for the treatment of cancer. The actual symptoms associated with cancer are well known and can be determined by a person of ordinary skill in the art by taking into account one or more factors, including, without limitation, the location of the cancer, the cause of the cancer, the severity of the cancer, and/or the tissue or organ affected by the cancer. Those of skill in the art will know the appropriate symptoms or indicators associated with a specific type of cancer and will know how to determine if an individual is a candidate for treatment as disclosed herein.

Exemplary forms of cancer which may be treated by the subject methods include, but are not limited to, leukemia, non-Hodgkin's lymphoma, prostate cancer, bladder cancer, lung cancer (including either small cell or non-small cell cancer), colon cancer, kidney cancer, liver cancer, breast cancer, cervical cancer, endometrial or other uterine cancer, ovarian cancer, skin cancer (e.g., melanoma), testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer.

In certain embodiments, a therapeutic compound disclosed herein reduces the size of a tumor by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other aspects of this embodiment, a therapeutic compound disclosed herein reduces the size of a tumor from, e.g., about 5% to about 100%, about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70%.

In certain embodiments, a cancer therapeutic disclosed herein is capable of reducing the number of cancer cells in an individual suffering from a cancer by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% as compared to a patient not receiving the same treatment. In other aspects of this embodiment, a cancer therapeutic is capable of reducing the number of cancer cells in an individual suffering from a cancer by, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% as compared to a patient not receiving the same treatment.

In certain embodiments, a therapeutically effective amount of a cancer therapeutic disclosed herein reduces or maintains a cancer cell population and/or tumor cell size in an individual by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 100%. In other aspects of this embodiment, a therapeutically effective amount of a cancer therapeutic disclosed herein reduces or maintains a cancer cell population and/or tumor cell size in an individual by, e.g., at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95% or at most 100%. In yet other aspects of this embodiment, a therapeutically effective amount of a cancer therapeutic disclosed herein reduces or maintains a cancer cell population and/or tumor cell size in an individual by, e.g., about 10% to about 100%, about 10% to about 90%, about 10% to about 80%, about 10% to about 70%, about 10% to about 60%, about 10% to about 50%, about 10% to about 40%, about 20% to about 100%, about 20% to about 90%, about 20% to about 80%, about 20% to about 20%, about 20% to about 60%, about 20% to about 50%, about 20% to about 40%, about 30% to about 100%, about 30% to about 90%, about 30% to about 80%, about 30% to about 70%, about 30% to about 60%, or about 30% to about 50%.

Compounds

The compounds herein described may have one or more asymmetric centers or planes. Compounds of the present invention containing an asymmetrically substituted atom may be isolated in optically active or racemic forms. It is well known in the art how to prepare optically active forms, such as by resolution of racemic forms (racemates), by asymmetric synthesis, or by synthesis from optically active starting materials. Resolution of the racemates can be accomplished, for example, by conventional methods such as crystallization in the presence of a resolving agent, or chromatography, using, for example a chiral HPLC column. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

The compounds herein described may have one or more charged atoms. For example, the compounds may be zwitterionic, but may be neutral overall. Other embodiments may have one or more charged groups, depending on the pH and other factors. In these embodiments, the compound may be associated with a suitable counter-ion. It is well known in the art how to prepare salts or exchange counter-ions. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Counter-ions may be changed, for example, by ion-exchange techniques such as ion-exchange chromatography. All zwitterions, salts and counter-ions are intended, unless the counter-ion or salt is specifically indicated. In certain embodiments, the salt or counter-ion may be pharmaceutically acceptable, for administration to a subject. Pharmaceutically acceptable salts are discussed later.

Pharmaceutical Compositions

Embodiments of the invention include pharmaceutical compositions of compounds shown in Table 1 and at least one pharmaceutically acceptable carrier or diluent. As used herein, pharmaceutical compositions include compositions suitable for administration to a subject or patient. As such, compositions do not include chemical reaction solutions or solutions used for screening assays, as these are not suitable for administration to a subject or patient. In some embodiments the compositions may include one or more than one compound from Table 1, one or more other pharmaceutically active agent, and may further contain other suitable substances and excipients, including but not limited to physiologically acceptable buffering agents, stabilizers (e.g. antioxidants), flavoring agents, agents to effect the solubilization of the compound, and the like.

In other embodiments, the composition may be in any suitable form such as a solution, a suspension, an emulsion, an infusion device, or a delivery device for implantation or it may be presented as a dry powder to be reconstituted with water or another suitable vehicle before use. The composition may include suitable pharmaceutically acceptable carriers and/or excipients.

In other embodiments, the compositions may comprise an effective amount of a modulator and/or other pharmaceutically active agent in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin.

In some embodiments, the compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed, A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In some embodiments, the compositions may be in a form suitable for administration by sterile injection. In one example, to prepare such a composition, the composition(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included, injectable solutions may also be prepared in which case appropriate stabilizing agents may be employed.

Formulations suitable for parenteral administration usually comprise a sterile aqueous preparation of the compound, which may be isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In some embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the active ingredient as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition may be in a form of nasal or other mucosal spray formulations (e.g. inhalable forms). These formulations can include purified aqueous solutions of the active compounds with preservative agents and isotonic agents. Such formulations can be adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared, for example, by incorporating the active compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the invention may further include one or more accessory ingredient(s) selected from encapsulants, diluents, buffers, flavoring agents, hinders, disintegrants, surface active agents, thickeners, lubricants, preservatives (including antioxidants), and the like.

In some embodiments, compositions may be formulated for immediate release, sustained release, delayed-onset release or any other release profile known to one skilled in the art.

In some embodiments, the pharmaceutical composition may be formulated to release the active compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action, by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the compound in a liposome or other encapsulate medium, or by fixation of the compound, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the compound may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

In all embodiments, the compound or other active compounds may be present as pharmaceutically acceptable salts or other derivatives, such as ether derivatives, ester derivatives, acid derivatives, and aqueous solubility altering derivatives of the active compound. Derivatives include all individual enantiomers, diastereomers, racemates, and other isomers of the compounds. Derivatives also include all polymorphs and solvates, such as hydrates and those formed with organic solvents, of the compounds. Such isomers, polymorphs, and solvates may be prepared by methods known in the art, such as by regiospecific and/or enantioselective synthesis and resolution.

The ability to prepare salts depends on the acidity or basicity of the compounds. Suitable salts of the compounds include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Unless the context clearly indicates otherwise, compositions of all embodiments can comprise various pharmaceutically acceptable salts, or other derivatives described above.

The formulation and preparation of such compositions are well known to those skilled in the art of pharmaceutical formulation. Formulations can be found in Remington: The Science and Practice of Pharmacy.

The amount of the compound employed in the present invention to be used varies according to the degree of the exposure to ionizing radiation encountered, and the stages of any radiation-induced damage. A suitable dosage is that which will result in concentration of the compound (in blood and/or tissues) sufficient to mitigate the damage of the ionizing radiation. The preferred dosage is that amount sufficient to render a subject asymptomatic after exposure to ionizing radiation.

The contents of all cited references (including literature references, issued patents, published patent applications) as cited throughout this application are hereby expressly incorporated by reference. The invention and the manner and process of making and using it, are described in such full, clear, concise and exact terms as to enable any person skilled in the art to which it pertains, to make and use the same.

The term "unit dosage form" or "unit" as used herein refers to physically discrete units suitable as unitary dosages for human and animal subjects, each unit containing a predetermined quantity of the compound calculated in an amount sufficient to produce the desired effect in association with a pharmaceutically acceptable, diluent, carrier or vehicle. The specifications for the novel unit dosage forms of the present invention depend on the particular compound employed and the effect to be achieved, and the pharmacodynamics associated with each compound in the subject.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

Dosing can be single dosage or cumulative (serial dosing), and can be readily determined by one skilled in the art. For instance, treatment may comprise a one-time administration of an effective dose of a pharmaceutical composition disclosed herein. Alternatively, treatment may comprise multiple administrations of an effective dose of a pharmaceutical composition earned out over a range of time periods, such as, e.g., once daily, twice daily, thrice daily, once every few days, or once weekly. The timing of administration can vary from individual to individual, depending upon such factors as the severity of an individual's symptoms. For example, an effective dose of a pharmaceutical composition disclosed herein can be administered to an individual once daily for an indefinite period of time, or until the individual no longer requires therapy. A person of ordinary skill in the art will recognize that the condition of the individual can be monitored throughout the course of treatment and that the effective amount of a pharmaceutical composition disclosed herein that is administered can be adjusted accordingly.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, the period of administration of a therapeutic compound is for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more. In certain embodiments, a treatment regimen may comprise a period during which administration is stopped for 1 day, 2 days, 3 days, 4 days, 5 days, 6 days, 7 days, 8 days, 9 days, 10 days, 11 days, 12 days, 13 days, 14 days, 3 weeks, 4 weeks, 5 weeks, 6 weeks, 7 weeks, 8 weeks, 9 weeks, 10 weeks, 11 weeks, 12 weeks, 4 months, 5 months, 6 months, 7 months, 8 months, 9 months, 10 months, 11 months, 12 months, or more.

The patient receiving this treatment is any animal in need, including primates, in particular humans, and other mammals such as equines, cattle, swine and sheep; and poultry and pets in general.

In other embodiments, the compound of Formula I or II may be provided with the one or more additional therapeutic agents in a kit, e.g., as separate pharmaceutical formulations capable of being used together in a conjoint therapy as discussed herein, either together in a single container or in separate containers. In certain such embodiments, the kit may further include instructions for the conjoint administration of the pharmaceutical formulations, e.g., for treating or preventing any of the conditions discussed above.

Such combination products may employ compounds of this invention, or pharmaceutically acceptable salts thereof within the dosage range described hereinbefore and the other pharmaceutically-active agent within its approved dosage range.

The invention now being generally described, it will be more readily understood by reference to the following examples which are included merely for purposes of illustration of certain aspects and embodiments of the present invention, and are not intended to limit the invention.

EXAMPLES

Example 1

The structures of 12 4-nitrophenylsulfonylpiperazines (NPSPs) or 4-nitrophenylsulfonamides (NPSs) are shown. See Table 1

TABLE 1

The structures of 12 NPSPs or NPSs of the invention

| Compound | Compound ID | Compound Structure | Compound Name |
|---|---|---|---|
| 1 | 5348300 | (structure) | 1-(4-fluorophenyl)-4-[(4-nitrobenzene)sulfonyl]piperazine |
| 2 | 5355512 | (structure) | 1-[(4-nitrobenzene)sulfonyl]-4-phenylpiperazine |
| 3 | 5346360 | (structure) | 1-(3-chlorophenyl)-4-(4-nitrobenzene)sulfonyl)piperazine |
| 4 | 5347486 | (structure) | 1-[(4-nitrobenzene)Sulfonyl]-4-[(2E)-3-phenylprop-2-en-1-yl]piperazine |
| 5 | 5116319 | (structure) | N,N-diethyl-4-nitrophenyl-1-sulfonamide |
| 6 | 5475972 | (structure) | 3-((4-nitrophenyl)sulfonyl)-2-phenyltetrahydrothiophene |

TABLE 1-continued

The structures of 12 NPSPs or NPSs of the invention

| Compound | Compound ID | Compound Structure | Compound Name |
|---|---|---|---|
| 7 | 5344400 | 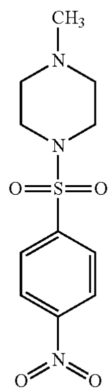 | 1-methyl-4-((4-nitrophenyl)sulfonyl)piperazine |
| 8 | 6561181 | 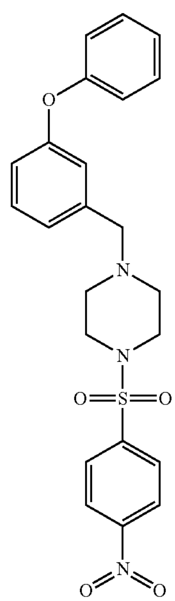 [SMILES: O=[N+]([O-])c1ccc(S(=O)(=O)N2CCN(Cc3cccc(Oc4ccccc4)c3)CC2)cc1] | 1-((4-nitrophenyl)sulfonyl)-4-(3-phenoxybenzyl)piperazine |
| 9 | 5243457 | 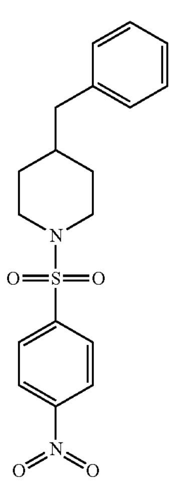 [SMILES: O=[N+]([O-])c1ccc(S(=O)(=O)N2CCC(Cc3ccccc3)CC2)cc1] | 4-benzyl-1-((4-nitrophenyl)sulfonyl)piperidine |
| 10 | 6571802 | | 1-(4-(methylthio)benzyl)-4-((4-nitrophenyl)sulfonyl)piperazine |
| 11 | AST5814142 | | 3-cyano,7-methyl-2-(4-((4-nitrophenyl)sulfonyl)piperazin-1-yl)quinoline |
| 12 | AST6538836 | | 3-cyano,7,8-dimethyl-2-(4-((4-nitrophenyl)sulfonyl)-1,4-diazepan-1-yl)quinoline |

Example 2

The ability of compounds from Example 1 to mitigate radiation-induced apoptosis in vitro relative to control values (100%) is shown in FIG. 1. Briefly, 100,000 small-molecules were screened at 30 µM final concentration in 1% dimethylsulfoxide (DMSO) using the viability of a murine lymphocyte line as a readout (Mitigation cell viability %). Ten thousand Til-1 murine lymphocyte cells were dispensed into each well of 384-well plates using a Multidrop 384 (Thermo Scientific, Waltham, Mass.) The Til-1 cells were irradiated at the dose of 2Gy. After 1 hour, the small-molecules were added. Twenty-four hours after the radiation, cell viability was assayed by luminesce-based measurement of ATP production (ATPlite, Perkin-Elmer, Waltham, Mass.) with a SpectraMax M5 microplate reader (Molecular Devices, Sunnyvale, Calif.). The Z' factor for the assay was >0.5. See Zhang, J. H., Chung, T. D., Oldenburg, K. R. "A Simple Statistical Parameter for Use in Evaluation and Validation of High Throughput Screening Assays," *J Biomol Screen* 4:67, 1999. A positive readout was ≤130% of the control irradiated value. Compounds 1-7 showed activity, including a 4-nitrophenyl sulfonamide derivative (Compound 5). This suggests a minimum moiety for efficacy. The piperazine group afforded additional efficacy beyond the common sulfonamide core suggesting that both moieties contribute although they were not in themselves sufficient for full activity. See FIG. 1.

Example 3

The top 5 performers from Example 1 were tested in vivo for their ability to mitigate against lethality from whole body irradiation. See Table 2.

Briefly, Animal Whole Body Irradiation (WBI) Assays were conducted with C3Hf/Kam and C57Bl6/J mice. The mice were bred and maintained in a strict gnotobiotic environment in the American Association of Laboratory Animal Care-Accredited Animal Facilities of Department of Radiation Oncology, UCLA. The Animal Care and Use Committee approved all experiments, which were performed in accordance with all local and national guidelines for the care and use of animals. Mice, 9-12 weeks old, were given WBI using a Gamma cell 40 irradiator (Cs137 source: Atomic Energy of Canada, Ltd.) at a dose rate of 67 Gy/min. Mice were monitored for at least 30 days and defined criteria for humane euthanasia was used as an endpoint.

Compounds were typically dissolved in 15 μL DMSO and suspended in 1 mL of 1% Cremphor EL in water for administration in 0.2 mL volumes. This amount of Cremophor did not significantly alter the response to WBI. All mice, including controls, received the same diluent as the experimental groups. The chosen compounds were administered to the mice 5 times at 24 h intervals, starting 24 hours after WBI at LD70/30 (7.725 Gy for the C3H strain) doses. Similar data were obtained with a single dose and at 48 hours after radiation exposure in both mouse strains. Both subcutaneous and oral routes were effective. The compounds provided greatly elevated animals survival level as compared to control group.

All 5 compounds were effective but Compound 2 (5355512) and Compound 3 (5346360) were effective at 5 mg/kg injected subcutaneously whereas the others required a greater quantity of the tested compound (e.g., 75 mg/kg). Indeed, Compound 2 and Compound 3 gave 100% survivors at day 30 at the lowest dosage of 5 mg/kg which was superior to the higher doses of 40 mg/kg and 75 mg/kg. See FIG. 2A-E.

TABLE 2

| Compound | Compound ID | In Vitro | Solubility (mol/L × $10^{-6}$) |
|---|---|---|---|
| 1 | 5348300 | 188% | 26.6 |
| 2 | 5355512 | 182% | 66.1 |
| 3 | 5346360 | 174% | 6.5 |
| 4 | 5347486 | 163% | 20.4 |
| 5 | 5116319 | 161% | 512.9 |

Example 4

Figure 3:
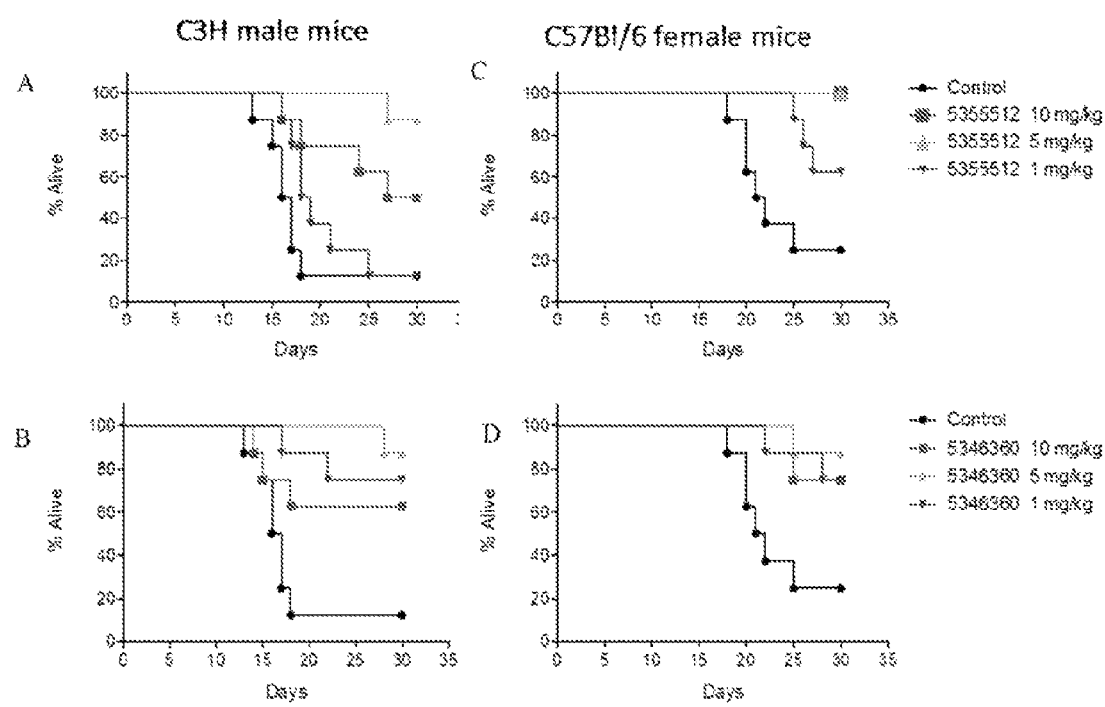
FIG. 3 shows the dose response experiments for compounds 2 (5355512) and 3 (5346360) in C3H male mice and C57Bl/6 female mice.
Figure 4:
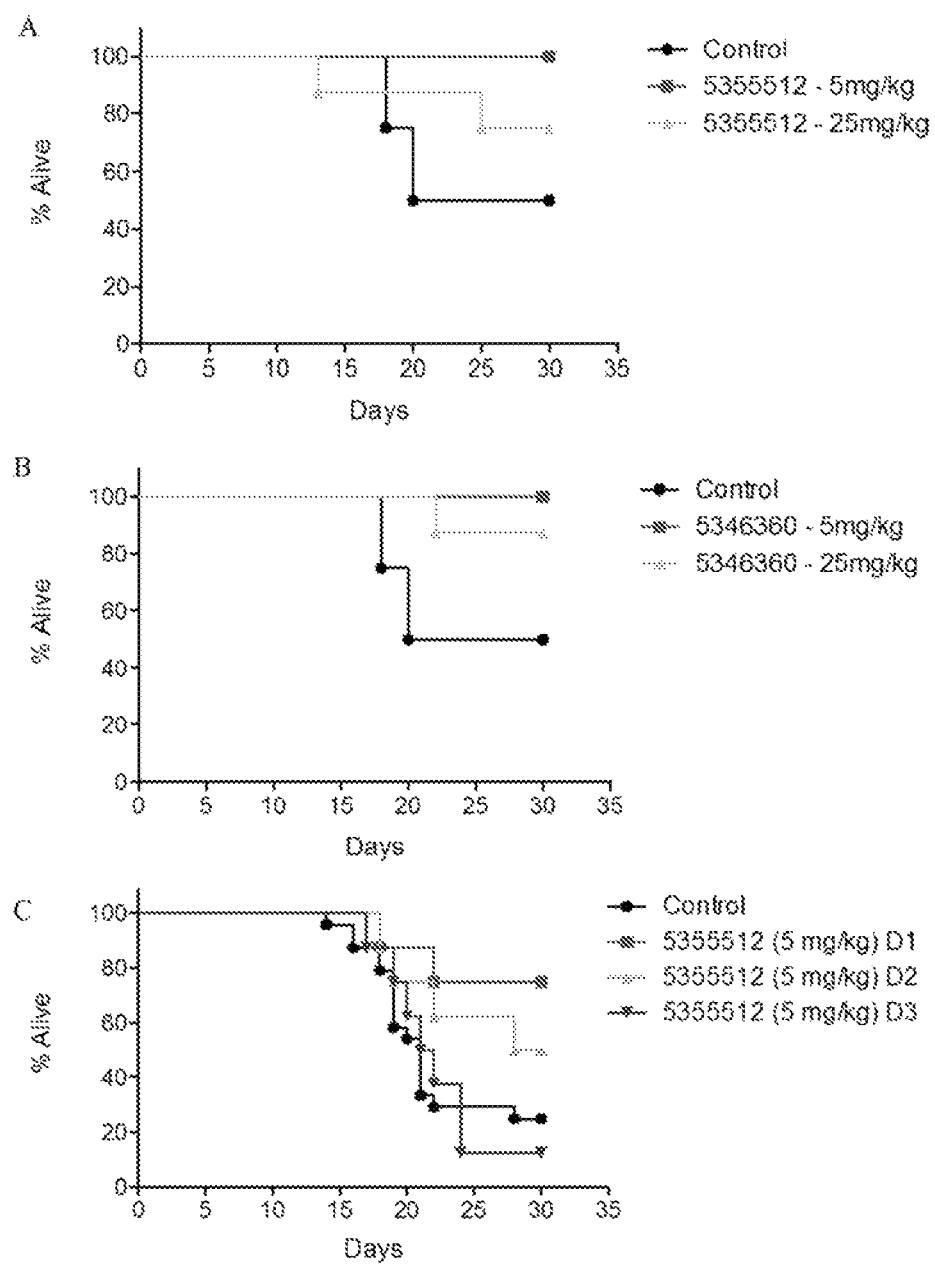
FIG. 4 shows the dose response experiments for compounds 2 (5355512) and 3 (5346360) when increased to 25 mg/kg (FIGS. 4A and 4B) and if dosing of compound 2 (5355512) was given after 24 hours (D1), 48 hours (D2), and 72 hours (D3) (FIG. 4C).
Figure 5:
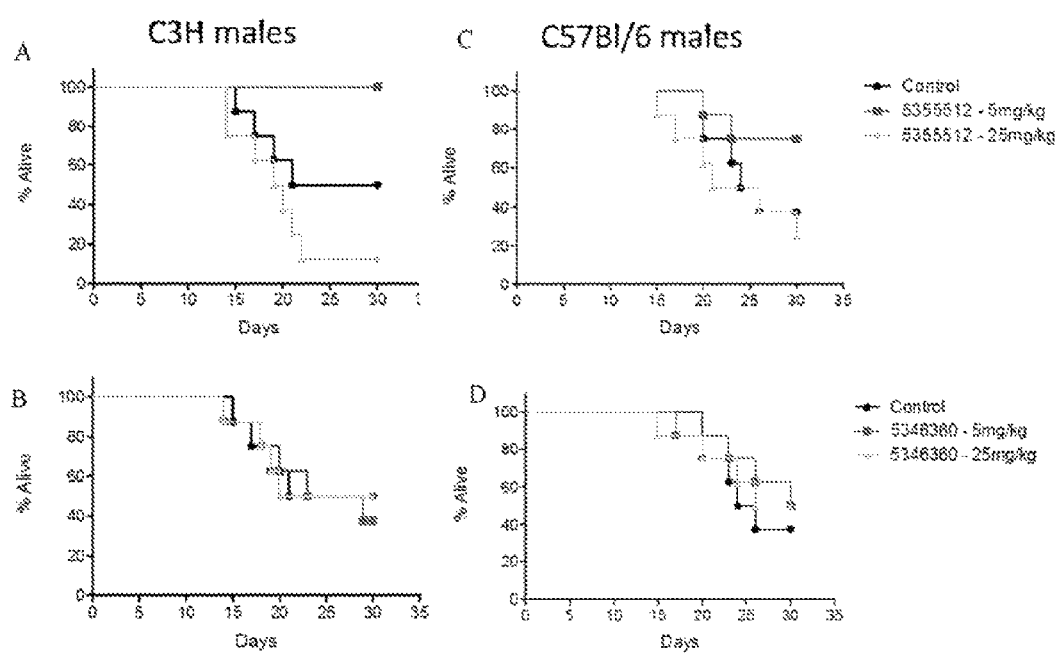
FIG. 5 shows the dose response when compounds 2 (5355512) and 3 (5346360) are given orally by gavage.

Dose response experiments were executed in a manner similar to the WBI Assay described in Example 3. These experiments indicated that 5 mg/kg was more, or as, effective, than 1, 2, 10, 40, or 75 mg/kg for both Compound 2 (5355512) and Compound 3 (5346360) in C3H male mice. See FIG. 3. Both Compound 2 (5355512) and Compound 3 (5346360) were effective in C57Bl/6 female mice in this case mitigating against LD70/30 doses of 8.509 Gy due to the relative radioresistance of this strain relative to C3Hs. A single dose of 5 mg/kg given 24 hours after WBI was effective (See FIGS. 4A and 4B) and increasing the dose to 25 mg/kg did not improve efficacy. Some activity was retained if a single dose was given 48, but not 72, hours after WBI (See FIG. 4C). When given orally by gavage, Compound 2 (5355512) in 5 daily doses starting at 24 hours post-WBI was effective at 5 mg/kg in both C3H and C57Bl/6 strains, but not at 25 mg/kg. (See FIG. 5) Interestingly, Compound 3 (5346360) given by the same gavage schedule was inactive in both strains at either dose.

Example 5

Figure 6:
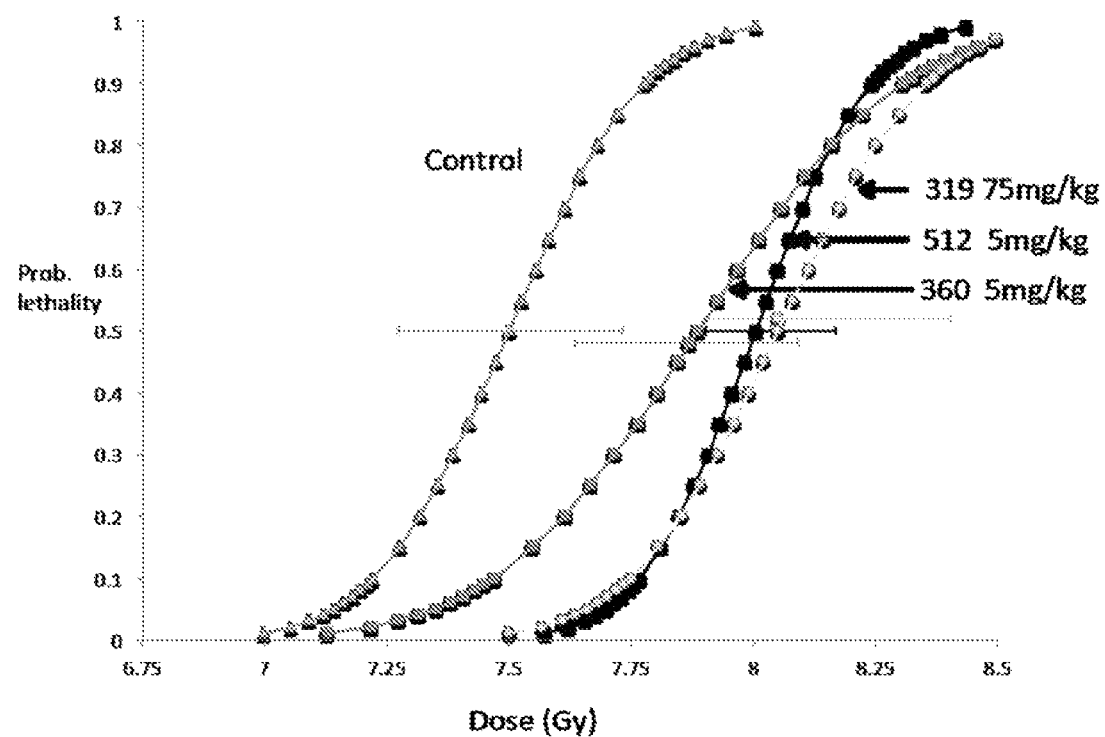
FIG. 6 shows the Probit analysis of the effect of varying the radiation dose with compounds 2 (5355512), 3 (5346360), and 5 (5116319).

Probit analyses of the effect of varying the radiation dose with Compound 2 (5355512) (5 mg/kg), and Compound 3 (5346360) (5 mg/kg), or 5 (5116319) (75 mg/kg) given subcutaneously for 5 days starting 24 hours after WBI, is shown in FIG. 6, with 95% confidence limits shown for LD50 values. The dose-response curves are steep with the dose modifying factors varying with the level of effect and drug, but were in the range 1.04-1.09. Such factors have to be considered against the level of the control and the reason for lethality. In this case, hematological insufficiency and not infection is the cause of death and as a result the radioresistance of the C3H strain is relatively high.

Example 6

Figure 7:
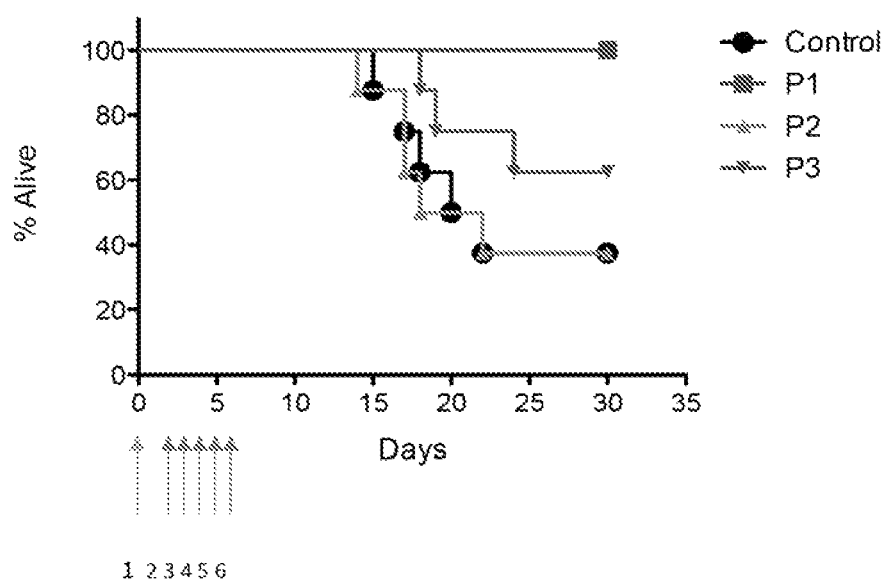
FIG. 7 shows the mitigation against whole body radiation lethality in vivo by analogs of Compound 2 (5355512).

Compounds P1, P2, and P3, analogs of Compound 2 (5355512), were synthesized according to standard protocols. See Table 3. The simplest NPSP (P1) was effective indicating that this was the optimum "core" structure. Interestingly, P1 is a natural breakdown product identified in vivo by mass spectrometry. WBI irradiation assays were conducted similar to those described in Example 3 except that compounds P1, P2, and P3 are soluble in water. The analogs were injected subcutaneously 5 times over 5 days at 5 mg/kg. Compound P2 elicited 100% survival after 30 days. See FIG. 7.

TABLE 3

Analogs of 5355512

| Compound ID | Structure |
|---|---|
| 5355512 | (structure shown) |

TABLE 3-continued

Analogs of 5355512

| Compound ID | Structure |
| --- | --- |
| Compound P1 | 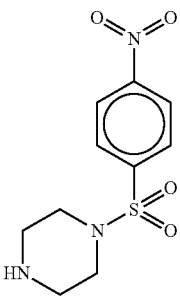 |
| Compound P2 | 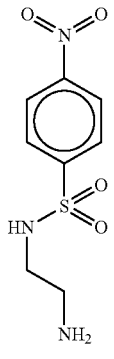 |
| Compound P3 | 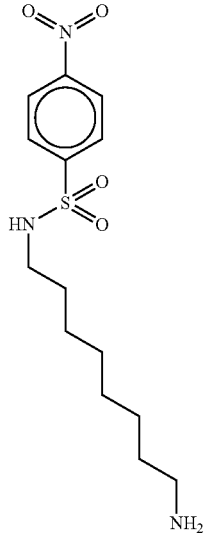 |

Example 7

Figure 8:
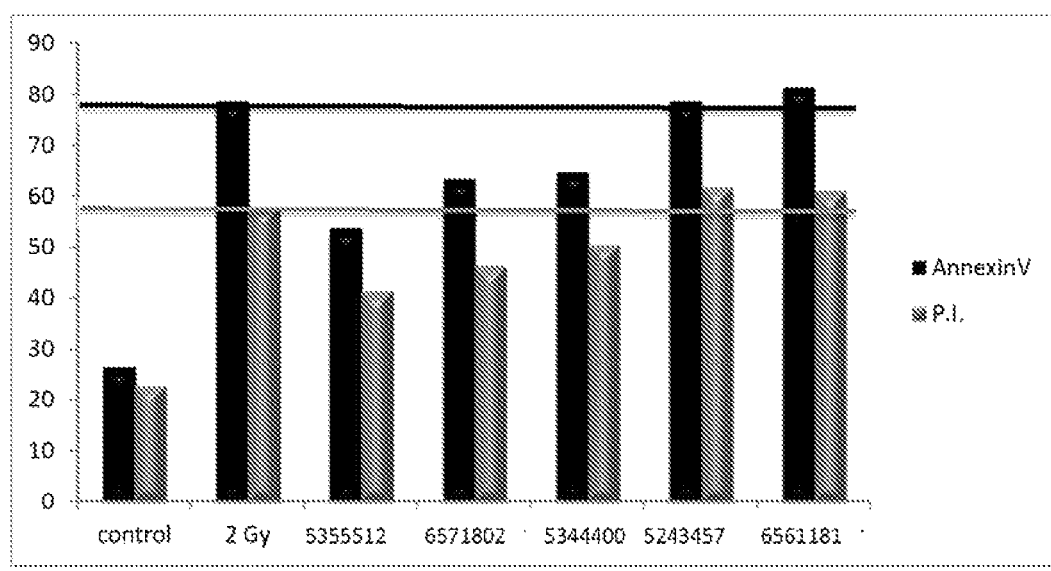
FIG. 8 shows the reduction in radiation induced apoptosis with the administration of certain compounds of the invention.
Figure 9:
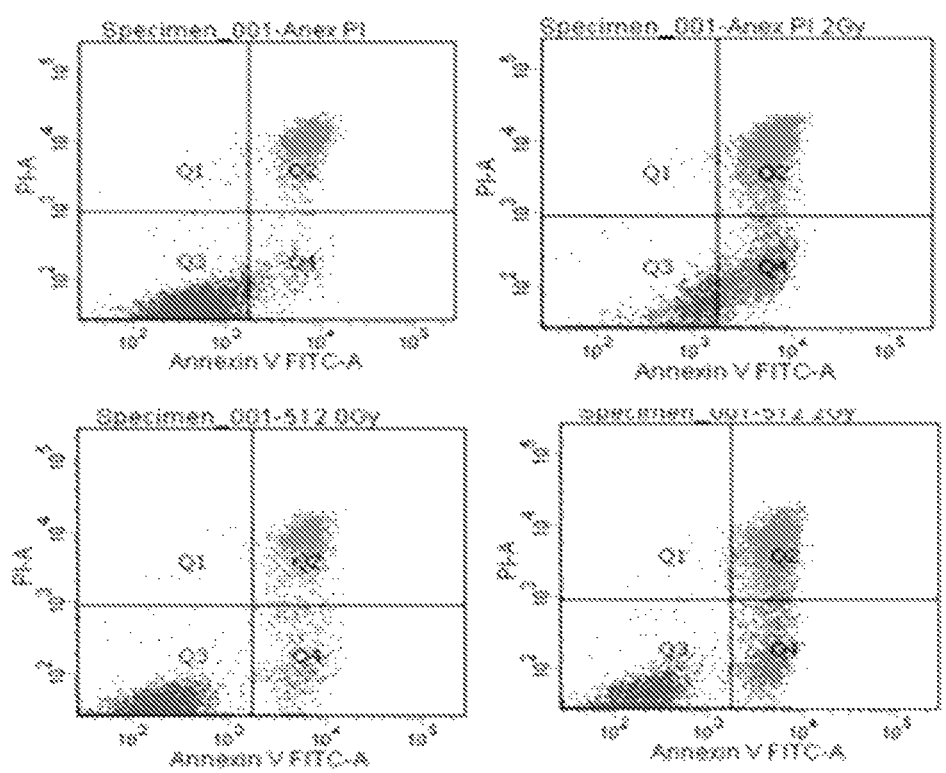
FIG. 9 shows flow cytometric assay results demonstrating the ability of active compounds to mitigate radiation-induced apoptosis relative to inactive compounds.

The ability of active compounds to mitigate radiation-induced apoptosis was confirmed relative to inactive compounds in a flow cytometric assay that employed annexin V for early stage apoptosis and propidium iodide for late stage apoptosis (BD BioSciences). (See FIGS. 8 and 9).

Example 8

Figure 10:
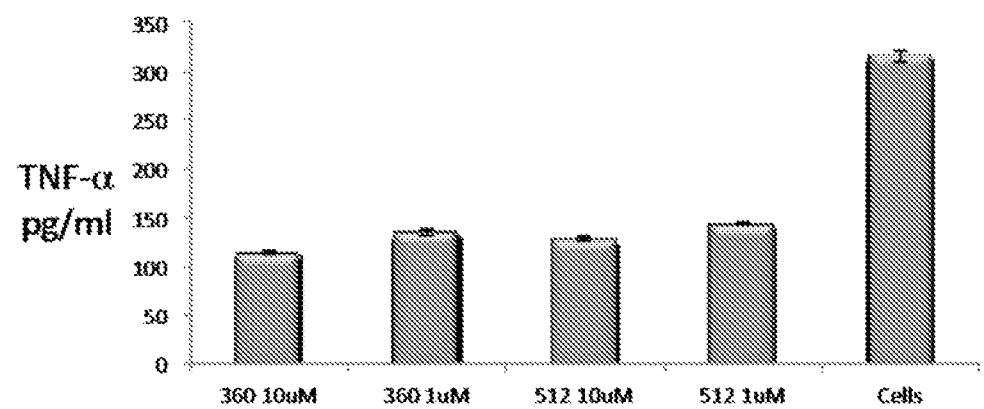
FIG. 10 shows that compounds 2 (5355512) and 3 (5346360) inhibit TNF-α production when added to stimulated peritoneal macrophages 1 hour after LPS measured by ELISA (FIG. 10A) and other compounds of the invention that were able to inhibit TNF-α production (FIG. 10B)
Figure 10:
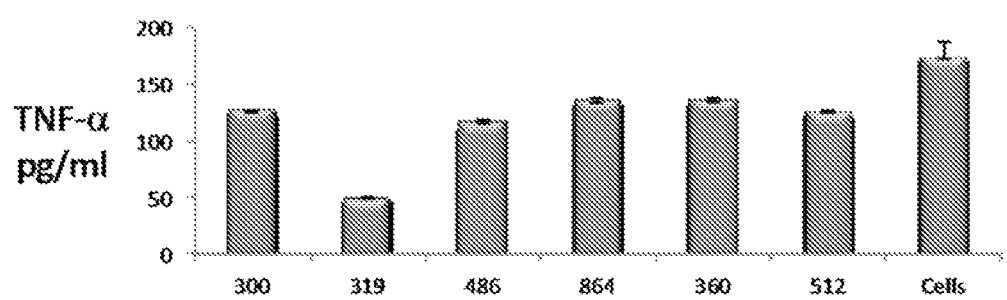

NPSPs were tested for their anti-inflammatory ability using murine macrophages. Compound 2 (5355512) showed anti-inflammatory activity being able to inhibit lipopolysaccharide (LPS)-induced production of tumor necrosis factor and other inflammatory cytokines. Briefly, peritoneal macrophages (PMs) were induced by intraperitoneal, injection of 150 µg MIS416 (Innate Immunotherapeutics, NZ) and harvested on day 4 by peritoneal wash out with PBS. Culture supernatants were harvested at 24 hrs and cytokines tested by ELISA (BD Biosciences, SD). Compound 2 (5355512) and Compound 3 (5346360) inhibit TNF-α production when added to stimulated peritoneal macrophages 1 hr after LPS measured by ELISA. See FIG. 10A. Additionally, all NPSPs and compound 5 (5116319) were able to inhibit TNF-α production. See FIG. 10B.

Figure 11:
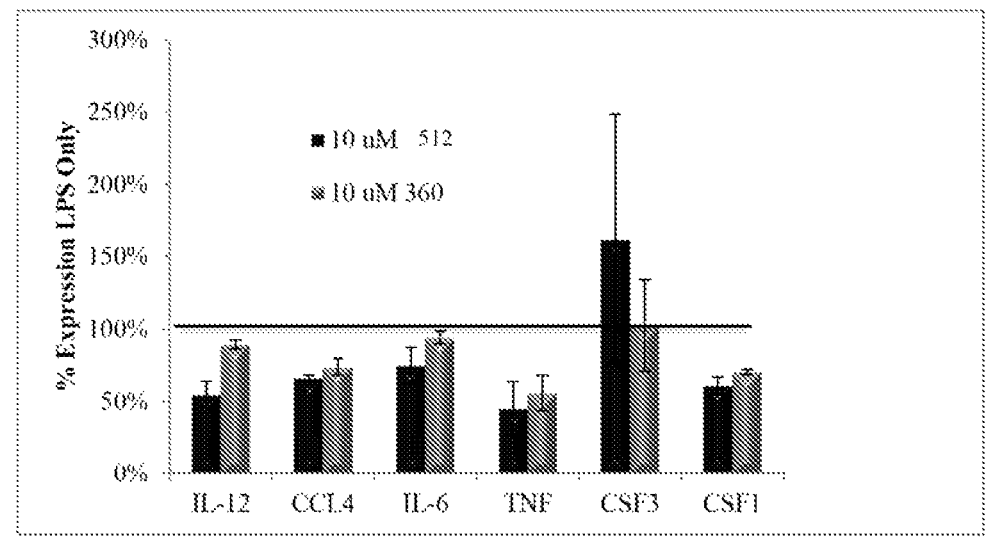
FIG. 11 shows that compounds 2 (5355512) and 3 (5346360) inhibit expression of TNF-α mRNA, and other cytokines, when added to bone marrow-derived macrophages 1 hour after LPS measured by RT-PCR.

Additionally, bone marrow-derived macrophages (BM-DMs) were derived by 7 days culture of marrow cells in medium containing 10% FBS and CSF-1 conditioned medium. The serum concentration was reduced to 2% FBS 16 h before stimulation with LPS for 30 min, treatment with drug and incubation for another 3.5 h (4 h total with LPS). Total cellular RNA was isolated by trizol and cDNA synthesized using iScript from BioRad. Gene expression was measured by qPCR and analyzed using the standard curve method, normalized to L32, Compound 2 (5355512) and Compound 3 (5346360) inhibit expression of TNF-α mRNA, and other cytokines, when added to bone marrow-derived macrophages 1 hr after LPS measured by RT-PCR. See FIG. 11.

In vivo, compound 2 (5355512) showed anti-inflammatory activity reflected by its ability to generate myeloid suppressor cells (data not shown).

Figure 12:
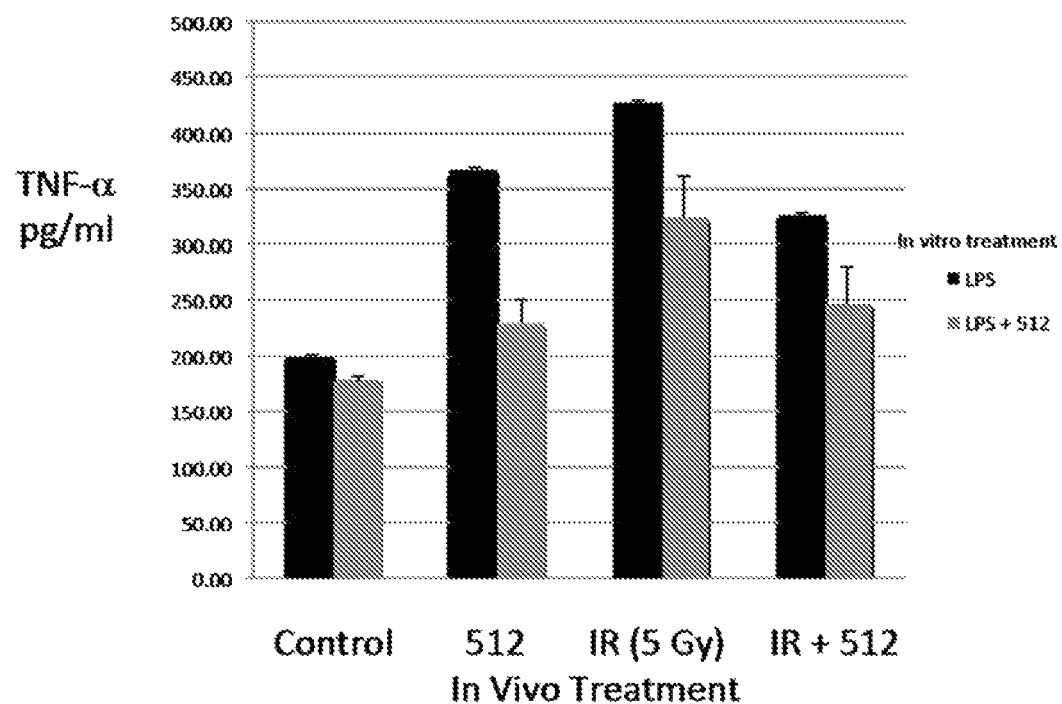
FIG. 12 shows how compound 2 (5355512) induces peritoneal macrophages to produce TNF-α in response to lipopolysaccharide (LPS).

To determine if compound 2 (5355512), injected subcutaneously would affect the activation status of induced peritoneal, macrophages, compound 2 (5355512) was given subcutaneously to control or WBI (5 Gy) and peritoneal macrophages harvested at day 4 as before. Cells from these groups of mice were incubated for 24 h with LPS or LPS then 512 (See FIG. 12). Surprisingly, treatment with Compound 2 (5355512) in vivo "primed" induced peritoneal cells to produce TNF-α in response to LPS to almost the same extent as WBI alone. However, this "priming" effect was less when WBI and Compound 2 (5355512) were combined in vivo. Also, in keeping with the data in FIGS. 10 and 11, the addition of Compound 2 (5355512) in vitro blunted TNF-α production.

Example 9

Figure 13:
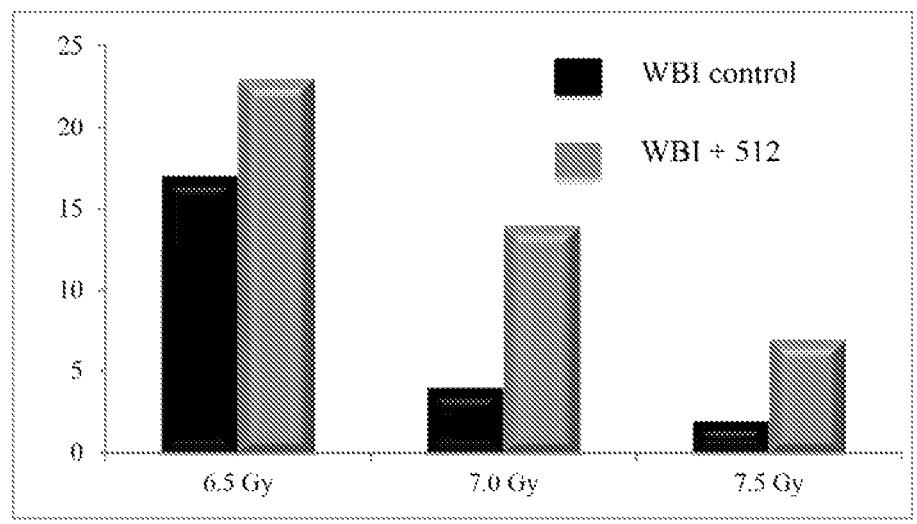
FIG. 13 shows that compound 2 (5355512) increases the total endogenous CFU in spleens (FIG. 13A) and average endogenous CPU per spleen (FIG. 13B) at 10 days after various doses of whole body irradiation (WBI).
Figure 13:
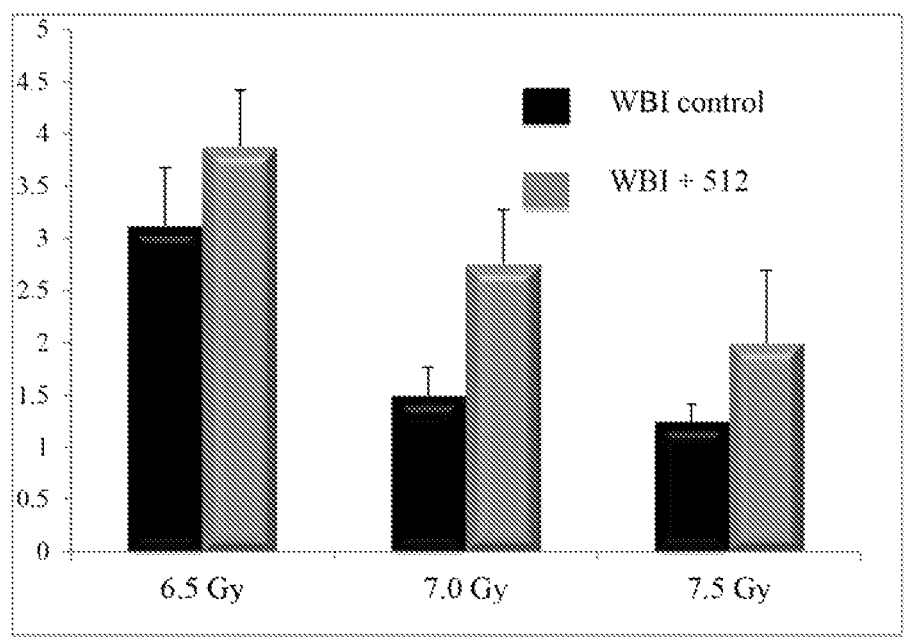

Compound 2 (5355512) also increased the number of endogenous colony forming units in the spleens of mice that had received LD70/30 radiation doses which is a measure of ability to generate hematopoietic stem cells and myeloid suppressors. The compounds increased survival when given 5 times at 24 hour intervals, starting 24 hours after abdominal or lung irradiation. For example, Compound 2 (5355512) increased the total endogenous CFU in spleens and average endogenous CFU per spleen at 10 days after whole body irradiation (WBI) at varying doses (e.g. 6.5 Gy 7.0 Gy, and 7.5 Gy). (See FIG. 13).

Example 10

Figure 14:
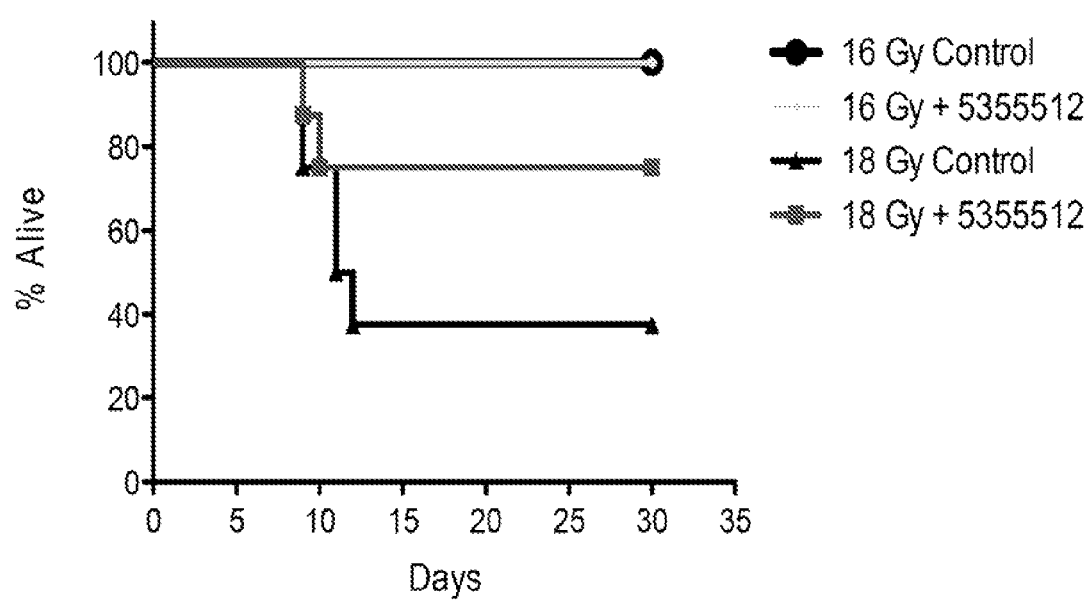
FIG. 14 shows the results of the in vivo assay with compound 2 (5355512) in C57Bl/6 mice who were irradiated with 16 and 18 Gy abdominally.
Figure 15:
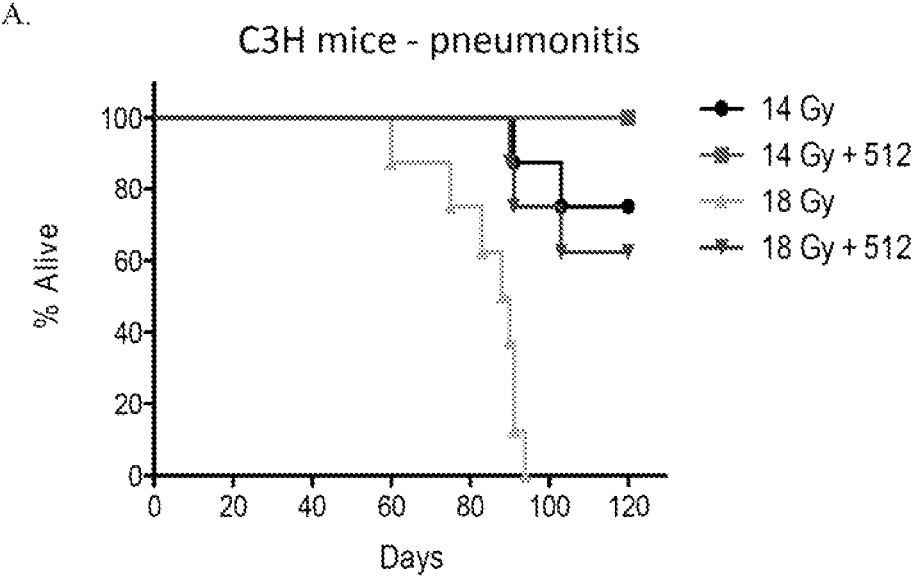
FIG. 15 shows the mitigation of radiation pneumonitis and fibrosis after local thoracic irradiation in C3H mice with pneumonitis (FIG. 15A) and C57Bl/6 mice with fibrosis (FIG. 15B).
Figure 15:
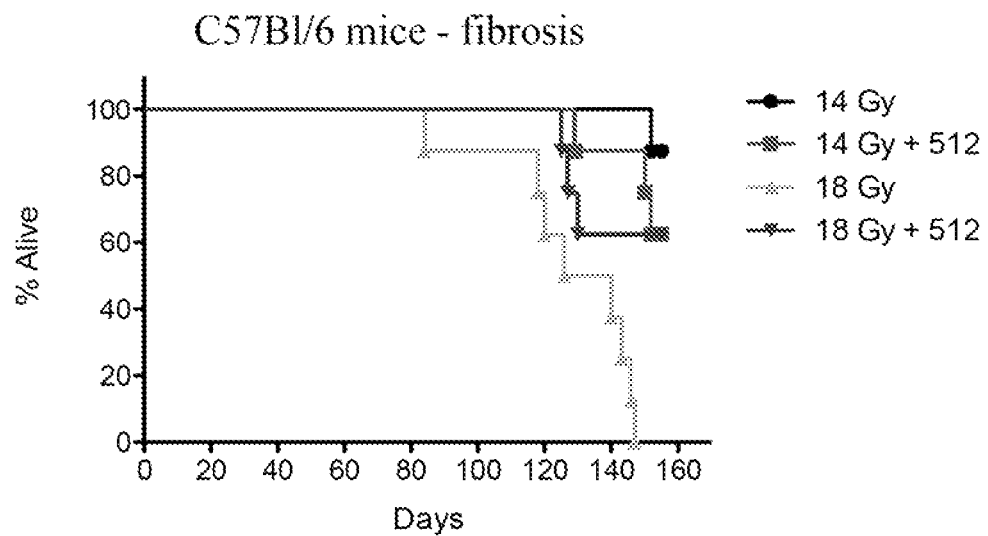

Further in vivo experiments similar to Example 3 were conducted except a localized radiation was used to demonstrate mitigation of abdominal radiation with compound 2 (5355512) at increased radiation doses. See FIG. 14 Additionally, in vivo experiments demonstrated mitigation of radiation pneumonitis and fibrosis after local thoracic irradiation. Addition of compound 2 (5355512) supported survival of C3H mice and C57 mice to 100 days post thoracic radiation (14 and 18 Gy). (See FIG. 15)

Example 11

Figure 16:
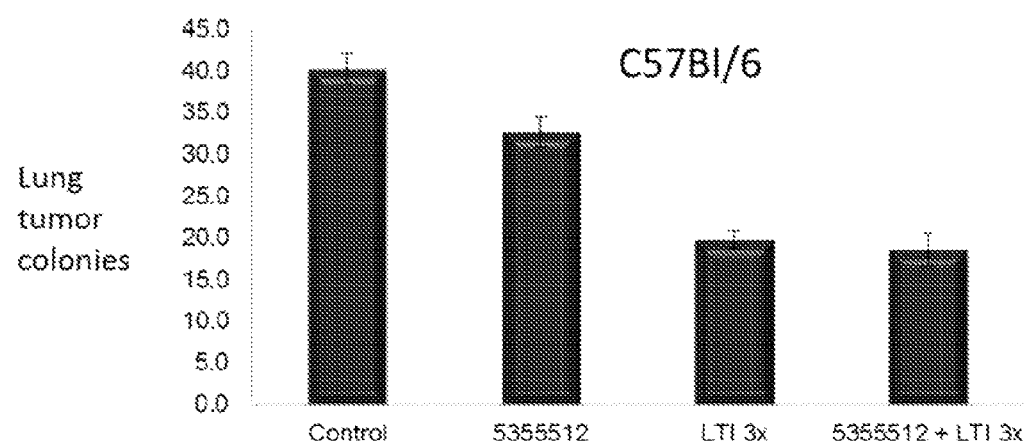
FIG. 16 shows the effects of the certain compounds of the invention on the growth of tumor lung colonies in vivo and on radiation response.
Figure 16:
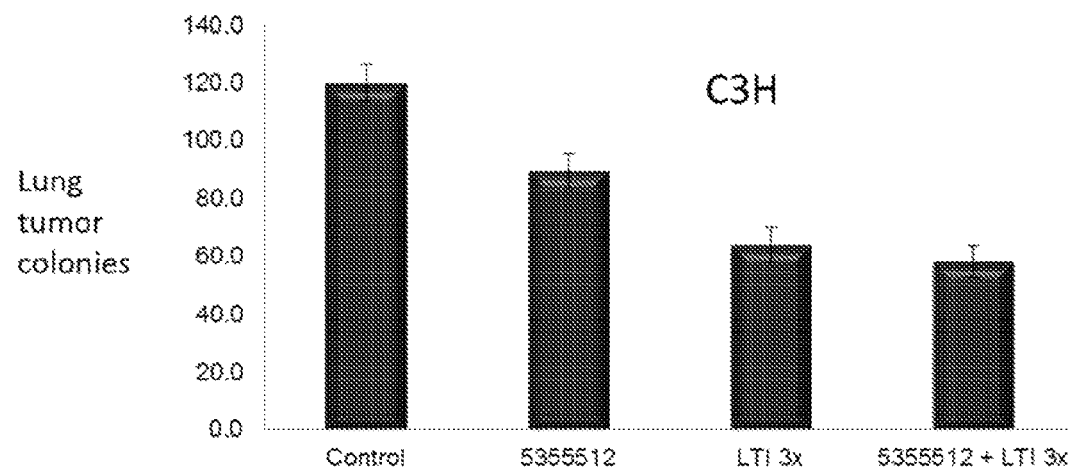

The Lewis lung (LLC) model of artificial metastasis was used to test the effects of the drug on the growth of tumor lung colonies in vivo and on radiation response. This was chosen because it is easy to see any drug effects on growth promotion and radioprotection in multiple tumors simultaneously. Specifically, C57Bl/6 mice and C3H mice were injected intravenously with $5 \times 10^4$ tumor cells. Subcutaneous injections of compound 2 (5355512) were started on day 4 when the tumors were already established in the lung. A daily dose of 20 mg/kg for 5 days was used to bias the experiment in favor of any tumor growth promotion. Local thoracic irradiation (LTI) was started on day 5 with 4 Gy daily doses for 3 days. This is higher than conventional 2 Gy to compensate for the rapid growth of murine tumors, but is still well within the higher ranges used clinically in hypofractionated exposures. The colonies were counted on day 14. FIG. 16 shows that compound 2 (5355512) significantly (P<0.05) decreased the number of lung tumor colonies assessed on day 14 by 20%. The colonies were also smaller in size. LTI alone decreased the number of colonies by 40%. This was not further decreased by the suboptimal drug treatment. Thus, compounds given to mice bearing Lewis Lung tumors decreased the number of tumor colonies that grew with and without lung irradiation demonstrating that the compounds did not protect tumors and indicating that they may be useful in patients receiving radiation therapy for cancer, protecting normal tissue from damage while exerting anti-tumor action.

As described herein, all embodiments or subcombinations may be used in combination with all other embodiments or subcombinations, unless mutually exclusive.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A method of mitigating an effect of ionizing radiation on a cell, organ, tissue, or organism, comprising contacting the cell, organ, tissue, or organism with a compound having the structure of Formula I:

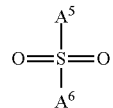

Formula I wherein:
$A^5$ is a secondary or tertiary amino substituent, and
$A^6$ is a substituted or unsubstituted aryl group.

2. The method of claim 1, wherein the compound contacts the cell before, during, or after exposure to ionizing radiation.

3. A method of treating inflammation in an organism, comprising administering to the organism a compound having the structure of Formula I:

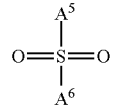

Formula I wherein:
$A^5$ is a secondary or tertiary amino substituent, and
$A^6$ is a substituted or unsubstituted aryl group.

4. A method of treating lung cancer in an organism, comprising administering to the organism a compound having the structure of Formula I:

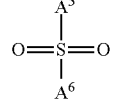

Formula I wherein:
$A^5$ is a secondary or tertiary amino substitutent, and
$A^6$ is a substituted or unsubstituted aryl group.

5. The method of claim 4, wherein the organism is a mammal.

6. A method of claim 1, wherein the aryl group of $A^6$ bears at least one substituent including a nitro substitutent.

7. The method of claim 6, wherein the nitro substituent is disposed at a position on $A^6$ distal to the sulfonyl.

8. The method of claim 7, wherein $A^6$ is optionally substituted 4-nitrophenyl.

9. The method of claim 1, wherein $A^5$ is a heterocyclic amine.

10. The method of claim 1, wherein $A^5$ is $NR^{15}R^{16}$, wherein each of $R^{15}$ and $R^{16}$, independently, is H, alkyl, alkenyl, alkynyl, aryl, heteroaryl, aralkyl, or heteroaralkyl, provided that $R^{15}$ and $R^{16}$ are not both H.

11. A method of claim 1, having the structure of Formula II:

Formula II

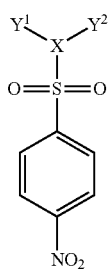

wherein:
X is N; and
$Y^1$ and $Y^2$ are each independently lower alkyl or $Y^1$ and $Y^2$ taken together with X form a heterocyclyl ring.

12. The method of claim 11, wherein $Y^1$ and $Y^2$ are each ethyl.

13. The method of claim 11, wherein $Y^1$ and $Y^2$ taken together form a piperazine ring.

14. The method of claim 11, wherein $Y^1$ and $Y^2$ taken together with X form:

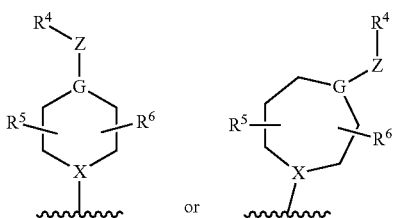

wherein
X is N;
G is selected from N or —C(H)—;
Z is absent or selected from substituted or unsubstituted alkyl, heteroalkyl, alkenyl, or alkynyl;
$R^4$ is absent or selected from substituted or unsubstituted aryl and heteroaryl; and
$R^5$ and $R^6$ are each independently absent or lower alkyl.

15. The method of claim 14, wherein G is N and $R^4$ is selected from phenyl, 4-fluorophenyl and 3-chlorophenyl.

16. The method of claim 14, wherein Z is absent.

17. The method of claim 14, wherein Z is prop-2-en-1-yl and $R^4$ is phenyl.

18. The method of claim 1, wherein the compound is selected from

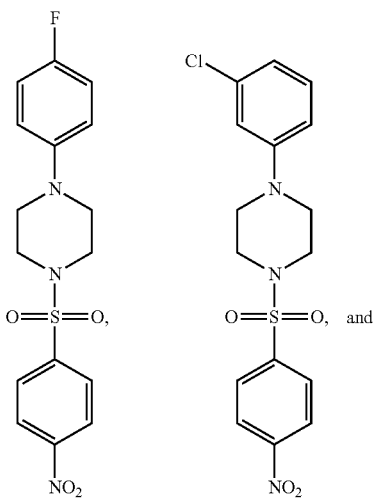

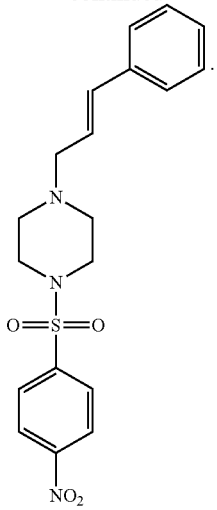

19. A method of claim 3, wherein the aryl group of $A^6$ bears at least one substituent including a nitro substitutent.

20. The method of claim 19, wherein the nitro substituent is disposed at a position on $A^6$ distal to the sulfonyl.

21. The method of claim 20, wherein $A^6$ is optionally substituted 4-nitrophenyl.

22. The method of claim 3, wherein $A^5$ is a heterocyclic amine.

23. The method of claim 3, wherein $A^5$ is $NR^{15}R^{16}$, wherein each of $R^{15}$ and $R^{16}$, independently, is H, alkyl, alkenyl, alkynyl, aryl, heteroaryl, aralkyl, or heteroaralkyl, provided that $R^{15}$ and $R^{16}$ are not both H.

24. A method of claim 3, having the structure of Formula II:

Formula I

wherein:
X is N; and
$Y^1$ and $Y^2$ are each independently lower alkyl or $Y^1$ and $Y^2$ taken together with X form a heterocyclyl ring.

25. The method of claim 24, wherein $Y^1$ and $Y^2$ are each ethyl.

26. The method of claim 24, wherein $Y^1$ and $Y^2$ taken together form a piperazine ring.

27. The method of claim 24, wherein $Y^1$ and $Y^2$ taken together with X form:

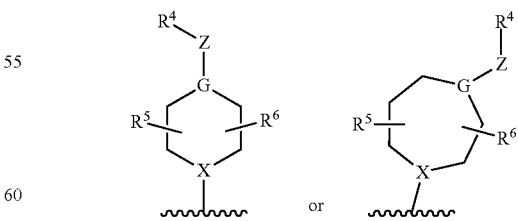

wherein
X is N;
G is selected from N or —C(H)—;
Z is absent or selected from substituted or unsubstituted alkyl, heteroalkyl, alkenyl, or alkynyl;

R[4] is absent or selected from substituted or unsubstituted aryl and heteroaryl; and R[5] and R[6] are each independently absent or lower alkyl.

28. The method of claim 27, wherein G is N and R[4] is selected from phenyl, 4-fluorophenyl and 3-chlorophenyl.

29. The method of claim 27, wherein Z is absent.

30. The method of claim 27, wherein Z is prop-2-en-1-yl and R[4] is phenyl.

31. The method of claim 3, wherein the compound is selected from

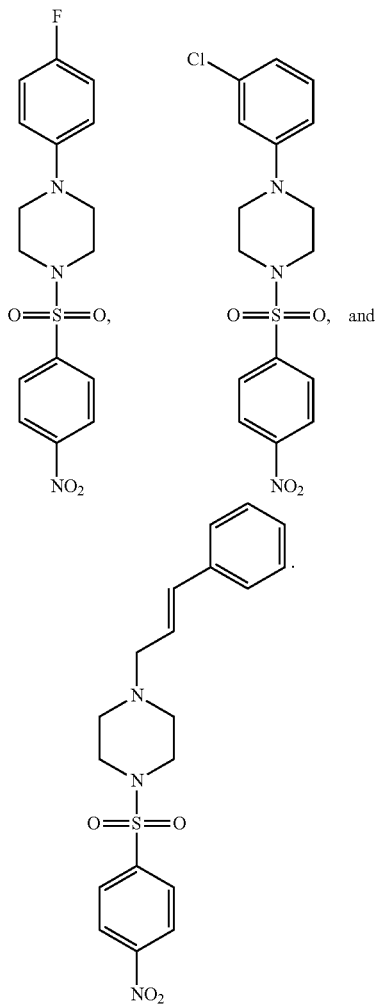

32. A method of claim 4, wherein the aryl group of A[6] bears at least one substituent including a nitro substitutent.

33. The method of claim 32, wherein the nitro substituent is disposed at a position on A[6] distal to the sulfonyl.

34. The method of claim 33, wherein A[6] is optionally substituted 4-nitrophenyl.

35. The method of claim 34, wherein A[5] is a heterocyclic amine.

36. The method of claim 4, wherein A[5] is NR[15]R[16], wherein each of R[15] and R[16], independently, is H, alkyl, alkenyl, alkynyl, aryl, heteroaryl, aralkyl, or heteroaralkyl, provided that R[15] and R[16] are not both H.

37. A method of claim 4, having the structure of Formula II:

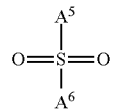

Formula I wherein:

X is N; and

Y[1] and Y[2] are each independently lower alkyl or Y[1] and Y[2] taken together with X form a heterocyclyl ring.

38. The method of claim 37, wherein Y[1] and Y[2] are each ethyl.

39. The method of claim 37, wherein Y[1] and Y[2] taken together form a piperazine ring.

40. The method of claim 37, wherein Y[1] and Y[2] taken together with X form:

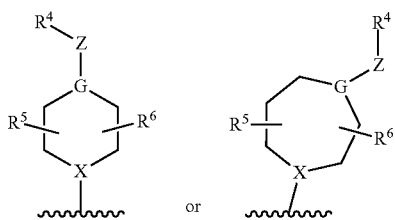

wherein

X is N;

G is selected from N or —C(H)—;

Z is absent or selected from substituted or unsubstituted alkyl, heteroalkyl, alkenyl, or alkynyl;

R[4] is absent or selected from substituted or unsubstituted aryl and heteroaryl; and R[5] and R[6] are each independently absent or lower alkyl.

41. The method of claim 40, wherein G is N and R[4] is selected from phenyl, 4-fluorophenyl and 3-chlorophenyl.

42. The method of claim 40, wherein Z is absent.

43. The method of claim 40, wherein Z is prop-2-en-1-yl and R[4] is phenyl.

44. The method of claim 4, wherein the compound is selected from

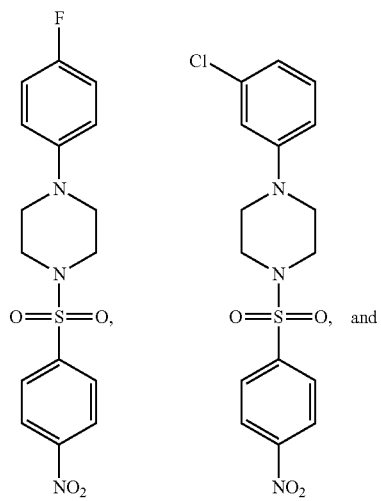

-continued
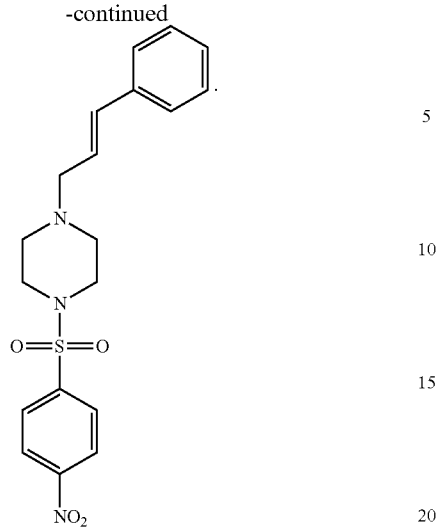
* * * * *

UNITED STATES PATENT AND TRADEMARK OFFICE
CERTIFICATE OF CORRECTION

PATENT NO. : 9,783,515 B2  
APPLICATION NO. : 14/889719  
DATED : October 10, 2017  
INVENTOR(S) : William McBride et al.

It is certified that error appears in the above-identified patent and that said Letters Patent is hereby corrected as shown below:

In the Claims

Column 40, between Lines 36-41, Claim 24, delete the following structure:

" Formula I " and replace with the following structure: -- Formula II --

Signed and Sealed this  
Twenty-fourth Day of April, 2018

Andrei Iancu  
*Director of the United States Patent and Trademark Office*

CERTIFICATE OF CORRECTION (continued)
U.S. Pat. No. 9,783,515 B2

Column 42, between Lines 1-8, Claim 37, delete the following structure:

" 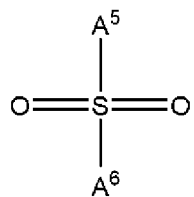 Formula I " and replace with the following structure: -- 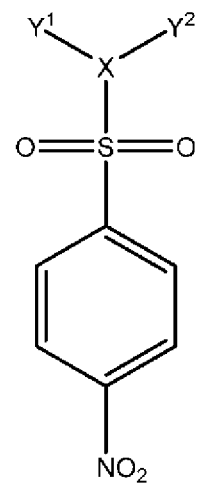 Formula II --